(12) United States Patent
Wampler et al.

(10) Patent No.: US 10,265,449 B2
(45) Date of Patent: Apr. 23, 2019

(54) ROTARY BLOOD PUMP

(71) Applicant: TC1 LLC, St. Paul, MN (US)

(72) Inventors: Richard K. Wampler, Loomis, CA (US); David M. Lancisi, Folsom, CA (US)

(73) Assignee: TC1 LLC, St. Paul, MN (US)

( * ) Notice: Subject to any disclaimer, the term of this patent is extended or adjusted under 35 U.S.C. 154(b) by 352 days.

(21) Appl. No.: 15/335,369

(22) Filed: Oct. 26, 2016

(65) Prior Publication Data

US 2017/0043076 A1 Feb. 16, 2017

Related U.S. Application Data

(63) Continuation of application No. 13/739,814, filed on Jan. 11, 2013, now Pat. No. 9,512,852, which is a
(Continued)

(51) Int. Cl.
*A61M 1/10* (2006.01)
*F04D 29/041* (2006.01)
(Continued)

(52) U.S. Cl.
CPC ......... *A61M 1/1036* (2014.02); *F04D 29/048* (2013.01); *F04D 29/0413* (2013.01);
(Continued)

(58) Field of Classification Search
CPC ............. F04D 29/0413; F04D 29/0473; F04D 29/2266; F04D 29/426; F04D 29/048;
(Continued)

(56) References Cited

U.S. PATENT DOCUMENTS 2,305,416 A 12/1942 Hansen, Jr.
3,114,582 A 12/1963 Milligan
(Continued)

FOREIGN PATENT DOCUMENTS

WO   WO 2000/032256   6/2000

OTHER PUBLICATIONS

United States Patent and Trademark Office, Notice of Allowance dated Jul. 26, 2016 in U.S. Appl. No. 13/739,814, 5 pages.
(Continued)

*Primary Examiner* — Igor Kershteyn
(74) *Attorney, Agent, or Firm* — Inskeep IP Group, Inc.

(57) ABSTRACT

The present invention provides a rotary blood pump with both an attractive magnetic axial bearing and a hydrodynamic bearing. In one embodiment according to the present invention, a rotary pump includes an impeller assembly supported within a pump housing assembly by a magnetic axial bearing and a hydrodynamic bearing. The magnetic axial bearing includes at least two magnets oriented to attract each other. One magnet is positioned in the spindle of the pump housing while the other is disposed within the rotor assembly, proximate to the spindle. In this respect, the two magnets create an attractive axial force that at least partially maintains the relative axial position of the rotor assembly. The hydrodynamic bearing is formed between sloping surfaces that form tight clearances below the rotor assembly.

22 Claims, 27 Drawing Sheets

Related U.S. Application Data continuation of application No. 11/694,761, filed on Mar. 30, 2007, now abandoned.

(60) Provisional application No. 60/787,738, filed on Mar. 31, 2006.

(51) Int. Cl.
| | |
|---|---|
| *F04D 29/047* | (2006.01) |
| *F04D 29/22* | (2006.01) |
| *F04D 29/42* | (2006.01) |
| *F04D 29/048* | (2006.01) |
| *A61M 1/12* | (2006.01) |

(52) U.S. Cl.
CPC ..... *F04D 29/0473* (2013.01); *F04D 29/0476* (2013.01); *F04D 29/2266* (2013.01); *F04D 29/426* (2013.01); *A61M 1/101* (2013.01); *A61M 1/1012* (2014.02); *A61M 1/1015* (2014.02); *A61M 1/1017* (2014.02); *A61M 1/1031* (2014.02); *A61M 1/122* (2014.02)

(58) Field of Classification Search
CPC . F04D 29/0467; A61M 1/101; A61M 1/1012; A61M 1/1015; A61M 1/1017; A61M 1/1031; A61M 1/122
See application file for complete search history.

(56) References Cited

U.S. PATENT DOCUMENTS

| | | |
|---|---|---|
| 3,243,238 A | 3/1966 | Lyman |
| 3,614,181 A | 10/1971 | Meeks et al. |
| 4,348,065 A | 9/1982 | Yoshioka et al. |
| 4,383,771 A | 5/1983 | Freytag et al. |
| 5,829,338 A | 11/1998 | Chrestoff et al. |
| 5,924,975 A * | 7/1999 | Goldowsky ........... F04B 17/046 600/16 |
| 6,183,220 B1 | 2/2001 | Ohara et al. |
| 6,250,880 B1 | 6/2001 | Woodard et al. |
| 6,394,769 B1 * | 5/2002 | Bearnson ............ F04D 13/0646 415/900 |
| 6,846,168 B2 | 1/2005 | Davis et al. |
| 7,976,271 B2 | 7/2011 | LaRose et al. |
| 2005/0025630 A1 * | 2/2005 | Ayre ..................... A61M 1/101 417/53 |
| 2005/0084399 A1 * | 4/2005 | Wampler .............. F04D 29/047 417/423.12 |
| 2007/0231135 A1 * | 10/2007 | Wampler ............ F04D 29/0413 415/229 |
| 2007/0280841 A1 * | 12/2007 | LaRose ................. A61M 1/101 417/423.12 |
| 2008/0240947 A1 * | 10/2008 | Allaire .................. A61M 1/101 417/420 |
| 2014/0241904 A1 * | 8/2014 | Yanai ........................ F04D 1/00 417/53 |
| 2014/0309481 A1 * | 10/2014 | Medvedev .......... A61M 1/1013 600/16 |
| 2017/0128644 A1 * | 5/2017 | Foster ................. A61M 1/1015 |

OTHER PUBLICATIONS

United States Patent and Trademark Office, Final Office Action dated Apr. 21, 2016 in U.S. Appl. No. 13/739,814, 9 pages.
United States Patent and Trademark Office, Office Action dated Aug. 28, 2015 in U.S. Appl. No. 13/739,814, 11 pages.
United States Patent and Trademark Office, Final Office Action dated Oct. 24, 2014 in U.S. Appl. No. 13/739,814, 24 pages.
United States Patent and Trademark Office, Office Action dated Jan. 6, 2014 in U.S. Appl. No. 13/739,814, 27 pages.

* cited by examiner

ROTARY BLOOD PUMP

RELATED APPLICATIONS

This application is a continuation of pending U.S. patent application Ser. No. 13/739,814 filed Jan. 11, 2013 entitled Rotary Blood Pump, which is a continuation of U.S. patent application Ser. No. 11/694,761 filed Mar. 30, 2007 entitled Rotary Blood Pump (now abandoned), which claims priority to U.S. Provisional Application Ser. No. 60/787,738 filed Mar. 31, 2006 entitled Rotary Blood Pump, all of which are hereby incorporated by reference in their entireties.

BACKGROUND OF THE INVENTION

Blood pumps remain particularly useful for the treatment of cardiac disease and especially heart failure. Typically, blood pumps are implanted within a patient and connected to the patient's circulatory system as a ventricular assist device or, in some circumstances, as an artificial heart. However, the fragile nature of blood and the absolute necessity of the pump's reliability have presented numerous obstacles to designing a more perfect blood pump.

For example, most blood pumps contain moving parts, such as an impeller, that force blood into and out of the pump housing. If these moving parts are not properly designed and adjusted, the blood passing through the pump can be damaged, causing hemolysis or thrombosis. Further, these moving parts can wear on each other, causing an increased likelihood of part failure and heat buildup that is imparted to the blood.

Two recent blood pump examples can be seen in U.S. Pat. No. 6,234,772 to Wampler, et al. and U.S. Pat. No. 6,250,880 to Woodard, et al. The Woodard patent illustrates a rotary blood pump that includes an impeller supported exclusively by a hydrodynamic bearing. The Wampler patent describes a rotary blood pump that includes both a hydrodynamic support bearing and a radial magnetic bearing that utilizes a repulsive magnetic force.

In the case of either patent, the impeller of the blood pump contains motor drive magnets disposed within the blades of the impeller. Electromagnets are positioned within the pump housing to generate a magnetic field that drives the rotation of the motor drive magnets and therefore the impeller.

Both blood pumps suffer from hydraulic inefficiencies due at least in part to the large, unconventional impeller blade geometry required for containing the motor rotor magnets. Further inefficiencies of these designs arise because of the natural attraction between the motor rotor magnets of the impeller and the back iron of the electromagnets. Additionally, these blood pump designs exclusively rely on hydrodynamic bearing for axial support, which can result in excessive shear forces that can damage the blood and cause medical complications in the patient's health.

In view of the above discussion, it is apparent that there is a need for a blood pump that overcomes the limitations of the prior art. Specifically, what is needed is a blood pump that reduces inefficiencies inherent in prior art pump designs that can lead to pump failure or blood damage.

OBJECTS AND SUMMARY OF THE INVENTION

It is an object of the present invention to overcome the limitations of the prior art.

It is a further object of the present invention to provide a rotary pump with a longer lifespan than prior art designs.

It is another object of the present invention to provide a rotary pump that minimizes damage to a patient's blood.

It is yet another object of the present invention to provide a rotary pump that includes reduced power consumption over prior art designs.

It is another object of the present invention to provide a rotary pump that more efficiently pumps blood through a circulatory system of a patient.

The present invention attempts to achieve these objects by providing a rotary blood pump with both a magnetic axial bearing and a hydrodynamic bearing. In one embodiment according to the present invention, a rotary pump includes a rotor assembly supported within a pump housing assembly by a magnetic axial bearing and a hydrodynamic bearing. The magnetic axial bearing includes at least two magnets oriented to attract each other. One magnet is positioned in the spindle of the pump housing while the other is disposed within the rotor assembly, proximate to the spindle. In this respect, the two magnets create an attractive axial force that at least partially maintains the relative axial position of the rotor assembly. The hydrodynamic bearing is formed between sloping surfaces that form tight clearances below the rotor assembly. As blood enters the pump, the hydrodynamic bearing produces upward axial force on the rotor assembly. Thus, the overall position of the rotor assembly is maintained during operation with minimal or no physical contact with the pump housing during operation.

One preferred embodiment of the present invention includes a pump housing defining a pump chamber having an inlet port and an outlet port; a rotor disposed within said pump housing; and an axial magnetic bearing disposed in said pump chamber to at least partially support said rotor, said axial magnetic bearing including a first magnet shaped such that a center of mass of said first magnet is offset from an axis of said axial magnetic bearing, said first magnet generating a magnetic force in a specified radial direction.

Another aspect of this preferred embodiment may further comprise a spindle and wherein said first magnet is disposed in said spindle.

In another aspect of this preferred embodiment said axial magnetic bearing further comprises a second magnet, said second magnet shaped such that a center of mass of said second magnet is aligned with said axis of said axial magnetic bearing, said second magnet being disposed in said rotor.

In another aspect of this preferred embodiment a cross-section of said first magnet is non-circular.

In another aspect of this preferred embodiment said non-circular cross-section of said first magnet is substantially a "D" shaped cross-section.

Another preferred embodiment of the present invention includes a blood pump comprising: a pump housing defining a pump chamber having an inlet port and an outlet port; a spindle disposed in said pump chamber; a rotor disposed in said pump housing and at least partially around said spindle, said rotor including a first magnet; and a second magnet disposed within said spindle, said second magnet shaped such that a center of mass of said second magnet is offset from an axis of said spindle so that said second magnet provides a reduced radial magnetic forces in a predetermined direction outward from said second magnet; wherein said first magnet and said second magnet comprise an axial magnetic bearing.

In another aspect of this preferred embodiment said center of mass of said first magnet is aligned with an axis of said rotor.

In another aspect of this preferred embodiment said first magnet is ring shaped.

In another aspect of this preferred embodiment said second magnet has a non-circular cross-sectional shape.

In another aspect of this preferred embodiment said first magnet includes poles oriented in an opposite direction of poles of said second magnet.

Another preferred embodiment of the present invention includes a method of compensating for radial bias in a blood pump comprising: providing a blood pump for circulating blood; rotating an impeller on an axial magnetic bearing within said blood pump so as to cause movement of blood through said blood pump, said movement of blood causing a radial bias on said rotor; producing a magnetic force having a substantially opposite direction and magnitude to said radial bias, said magnetic force being generated by a magnet shaped to have a center of mass spaced from an axis of said axial magnetic bearing.

In another aspect of this preferred embodiment the producing of said magnetic force includes providing a magnet having a non-circular cross-section.

In another aspect of this preferred embodiment the providing of a magnet having a non-circular cross-section comprises providing a magnet having a "D" shaped cross-section.

In another aspect of this preferred embodiment producing a force further comprises providing a spindle around which said impeller rotates and providing a magnet in said spindle.

Another preferred embodiment of the present invention includes a blood pump comprising: a housing assembly including an interior space; a rotor disposed in said interior space; an axial magnetic bearing consisting of: a first magnet disposed in said rotor and having a north pole and a south pole; and a second magnet disposed in said interior space near a center of said rotor and having a north pole and a south pole.

Another aspect of this preferred embodiment may further comprise a spindle disposed in said housing assembly and wherein said second magnet is disposed in a spindle.

In another aspect of this preferred embodiment said north pole and south pole of said first magnet is oriented in an opposite direction of said north pole and south pole of said second magnet.

Another aspect of this preferred embodiment may further comprise a position adjustment assembly coupled to said second magnet to modify a position of said second magnet relative to said first magnet.

Another preferred embodiment of the present invention includes a blood pump comprising: a housing assembly comprising a first housing member and a second housing member, said first housing member being formed from one continuous non-assembled piece of material; said housing members defining a pump chamber having an interior surface; a plurality of lifts formed integrally on an interior surface of said first housing member; said lifts providing a hydrodynamic bearing surface to a rotor during operation of said blood pump.

In another aspect of this preferred embodiment said first housing member includes a stator chamber.

In another aspect of this preferred embodiment said stator chamber comprises a removable access cover for selectively accessing said stator chamber from an exterior of said blood pump.

In another aspect of this preferred embodiment each of said plurality of lifts comprise an elongated sloping surface.

In another aspect of this preferred embodiment each of said plurality of lifts further comprise a shortened flat surface coextensive with said elongated sloping surface.

Another preferred embodiment of the present invention includes a blood pump comprising: a housing defining an interior pump chamber having an interior surface; a rotor disposed within said interior pump chamber; said interior surface beneath said rotor being formed from a continuous, non-assembled material that constitutes a lower portion of said housing and having a plurality of lifts integrally formed from said interior surface, said lifts forming a hydrodynamic bearing with a bottom surface of said rotor.

Another aspect of this preferred embodiment may further comprise a stator chamber accessible from an exterior of said blood pump.

In another aspect of this preferred embodiment said lifts are comprised of an elongated sloping surface.

In another aspect of this preferred embodiment said lifts are further comprised of a shortened flat surface coextensive with said elongated sloping surface.

Another preferred embodiment of the present invention includes a blood pump comprising: a housing assembly, an impeller disposed in said housing assembly a pump chamber formed from said housing assembly, said pump chamber having an inlet and an outlet; and an outlet flow path including a first groove positioned around a circumference of the pump chamber forming a torus shape and a second groove connecting to said first groove and said outlet; said second groove having a size larger than a size of said first groove; said first groove sized so as to throttle flow upstream of said outlet and thereby cause a leakage flow between said impeller and said housing assembly.

In another aspect of this preferred embodiment said second groove progressively increases in size towards said outlet.

In another aspect of this preferred embodiment said leakage flow is between said impeller and a spindle of said housing assembly.

In another aspect of this preferred embodiment said second groove cooperates with said body to form an outlet passage in communication with said outlet.

Another preferred embodiment of the present invention includes a blood pump comprising: a pump housing defining a pump chamber having an inlet port and an outlet port; a rotor disposed within said pump housing; and a torus-shaped volute defined by said pump housing; said volute circumferentially disposed around said pump chamber and forming an outlet passage in communication with said outlet port and increasing in diameter towards said outlet port; said torus-shaped volute having a size that throttles fluid flow upstream of said outlet port and thereby cause a leakage flow between said rotor and said pump housing.

In another aspect of this preferred embodiment said volute is disposed around the entire circumference of said pump chamber.

In another aspect of this preferred embodiment said volute is comprised of matching grooves of mating portions of said pump housing.

In another aspect of this preferred embodiment said outlet passage has a generally circular cross section.

Another preferred embodiment of the present invention includes a method of pumping blood comprising: providing a pump housing defining a pump chamber moving blood from an inlet in said pump housing through an impeller of said pump chamber to an outlet in said pump housing; and increasing the pressure of said blood in said pump chamber upstream of said outlet so as to force a leakage flow blood between mating surfaces of said impeller and said pump housing.

In another aspect of this preferred embodiment said increasing of the pressure of said blood in said pump chamber comprises passing blood through a throttling volute in said pump chamber.

In another aspect of this preferred embodiment passing blood through a throttling volute in said pump chamber comprises passing blood through said volute having a diameter between about 2-5 mm.

In another aspect of this preferred embodiment passing blood through a throttling volute in said pump chamber comprises increasing the pressure inside the pump relative to the outlet between about 50% and about 100%.

Another preferred embodiment of the present invention includes a blood pump comprising: a pump housing defining a pump chamber having an inlet and an outlet; a rotor rotatably disposed in said pump chamber; and at least one lift positioned on a surface of said pump chamber to create a hydrodynamic bearing surface with said rotor; said lift including a first surface extending at an angle from said pump chamber and a second surface connected to said first surface and extending substantially parallel to said surface of said pump chamber; wherein said first surface is at least longer than said second surface.

Another aspect of this preferred embodiment may further comprise a plurality of lifts.

In another aspect of this preferred embodiment said first surface is angled from said surface of said pump chamber is between about 0.5 degrees and about 3 degrees.

DETAILED DESCRIPTION OF THE INVENTION

Figure 1:
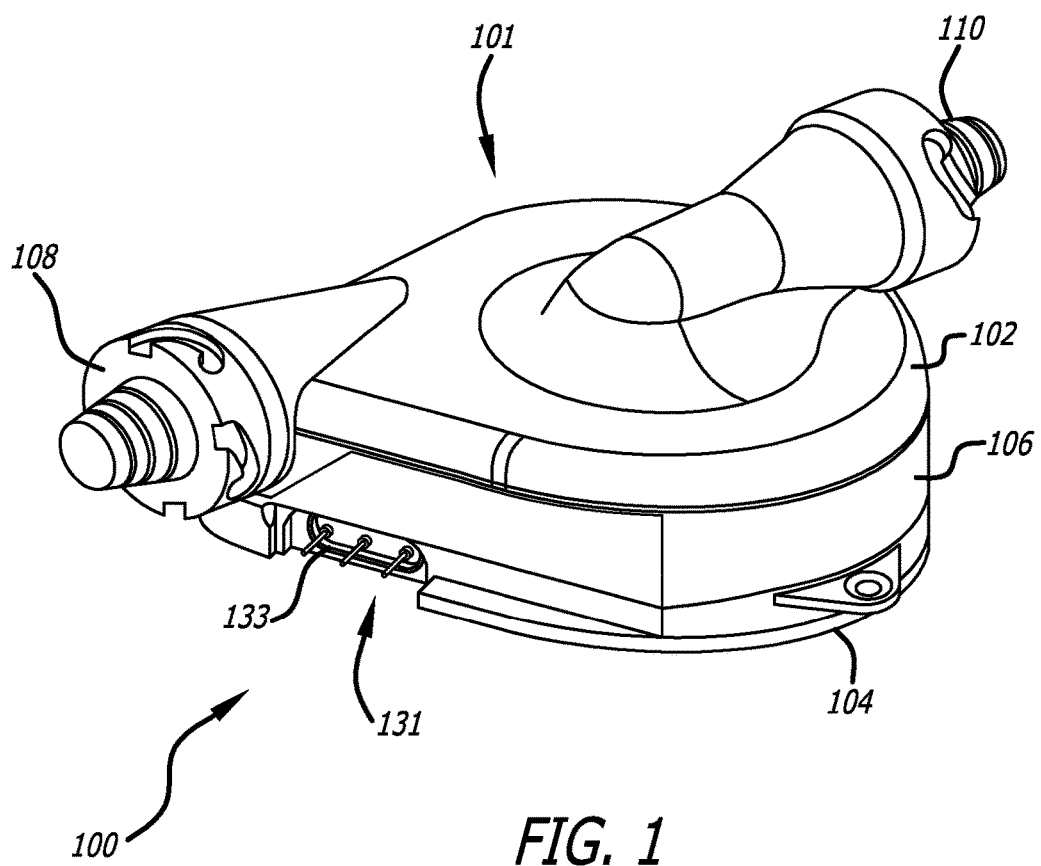
FIG. 1 illustrates a perspective view of a rotary blood pump according to the present invention.

FIG. 1 illustrates a preferred embodiment of a rotary blood pump 100 according to the present invention. The rotary blood pump 100 is coupled to the circulatory system of a patient, allowing blood to enter through an inlet 110 then exit a short time later through an outlet 108.

Figure 2:
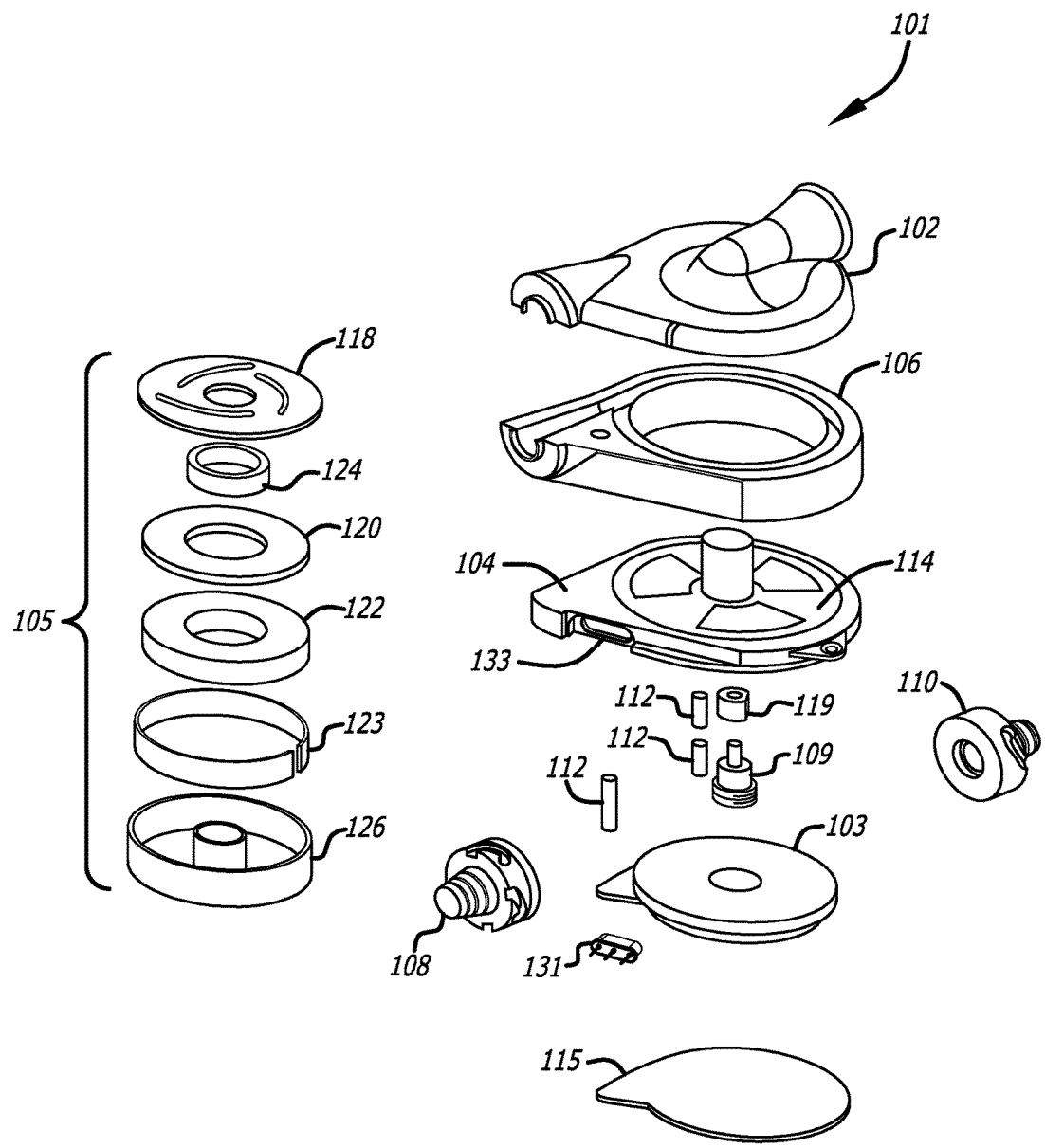
FIG. 2 illustrates an exploded view of the blood pump of FIG. 1.

Blood is primarily driven through the rotary blood pump 100 by a rotor assembly 105 within a housing assembly 101, as seen in FIG. 2. The rotor assembly 105 is not physically connected to the housing assembly 101. Instead, the rotor assembly 105 is supported by an axial hydrodynamic bearing created between a thrust plate 114 and a bottom surface of the rotor assembly 105, a radial hydrodynamic bearing between the inside diameter of the rotor assembly 105 and the outside diameter of the spindle portion of the thrust plate 114 (or, in the alternative, between the outside of the rotor assembly 105 and the inside diameter of the housing assembly 101), and by an axial magnetic bearing created between a spindle magnet 119 and a rotor axial magnet 124. The nature of these bearings is discussed in detail in U.S. application Ser. No. 10/940,419 entitled Rotary Blood Pump which is incorporated herein by reference. Thus, during operation, contact between the rotor assembly 105 and the housing assembly 101 are minimized and, in one embodiment, even reduced to zero contact, thereby reducing friction, minimizing heat generation, and decreasing power requirements over prior art designs.

Turning to FIG. 2, this exploded view illustrates three main assemblies that makeup the rotary blood pump 100: the pump housing assembly 101, a motor assembly 103 and the rotor assembly 105.

Figure 3A:
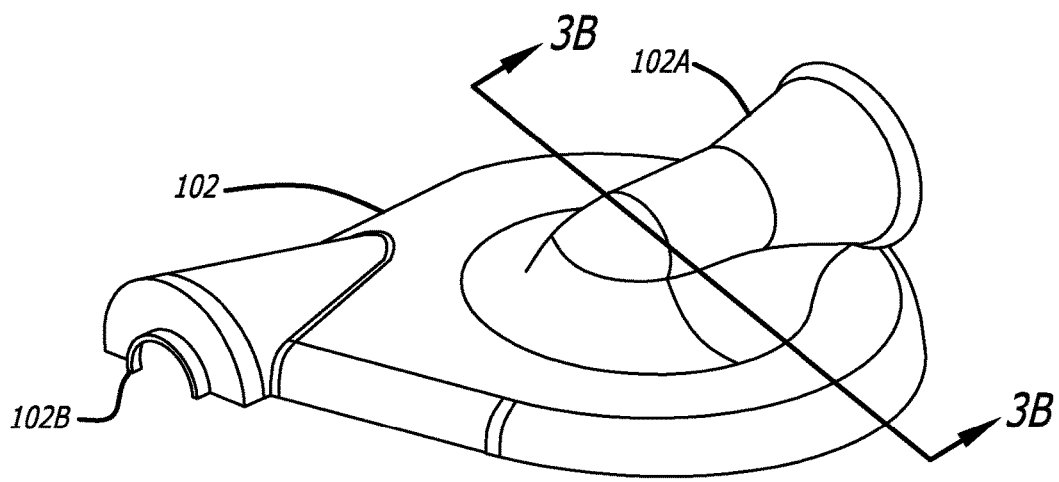
FIG. 3A illustrates a perspective view of a housing top according to the present invention.
Figure 3B:
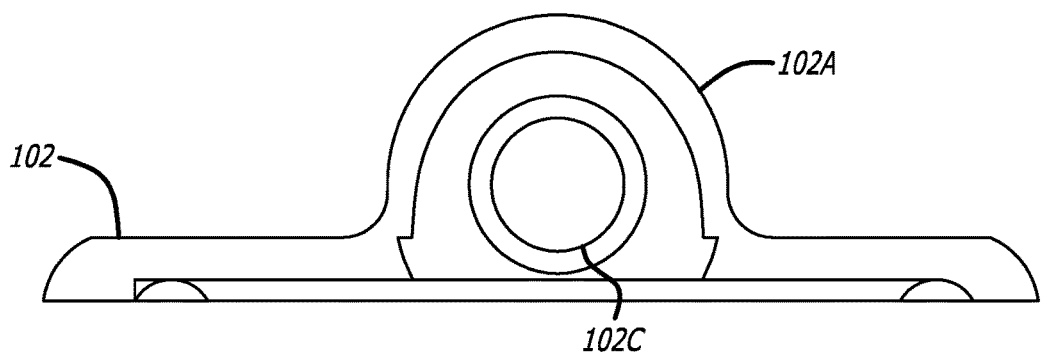
FIG. 3B illustrates a profile view of the housing top of FIG. 3A along line 3B-3B of FIG. 3A.

Generally speaking, the pump housing assembly 101 makes up the main body of the rotary blood pump 100, including a housing top 102 and a housing bottom 104 which fastens by welding and aligned by alignment pins 112 to a top and bottom side of a housing middle 106. FIG. 3A illustrates a perspective view of the housing top 102 including an outlet passage 102B partially positioned through a side area. FIG. 3B shows a profile view of the housing top 102, having a raised area 102A that accommodates an inlet passage 102C.

Figure 4A:
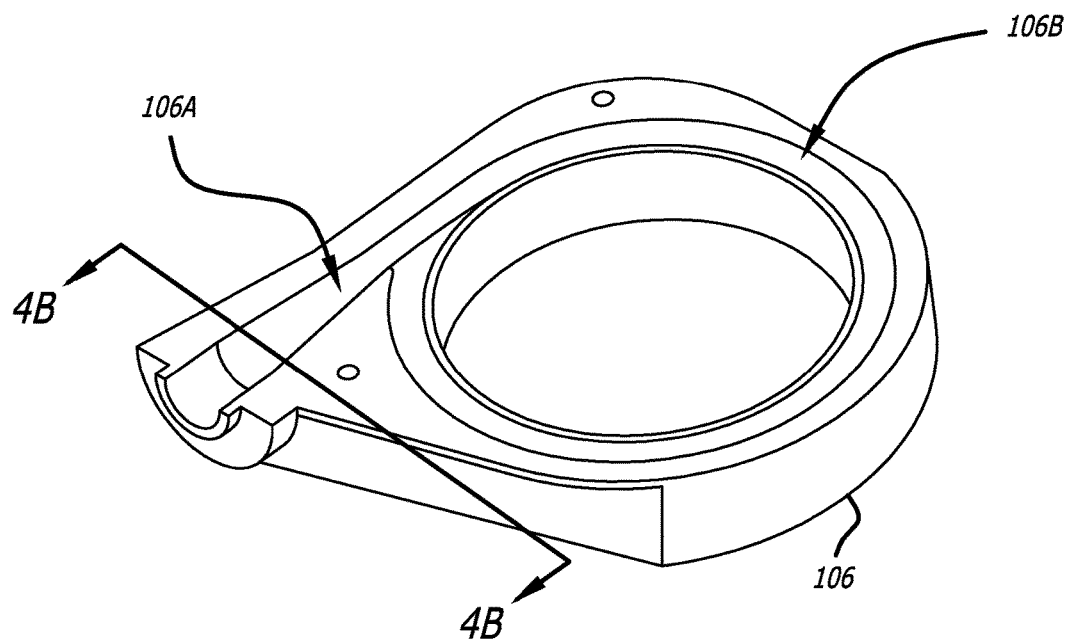
FIG. 4A illustrates a perspective view of a housing middle according to the present invention.
Figure 4B:
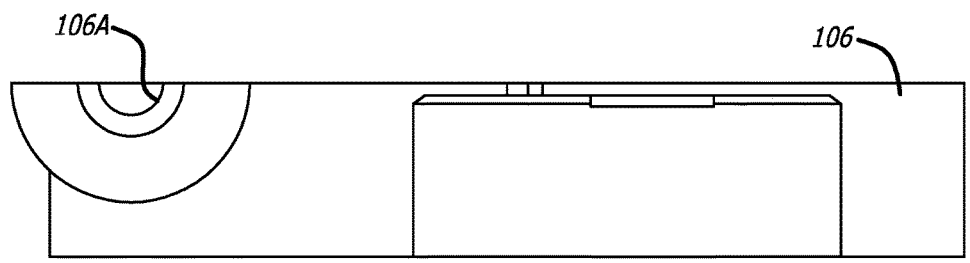
FIG. 4B illustrates a profile view of the housing middle of FIG. 4A along line 4B-4B of FIG. 4A.
Figure 4C:
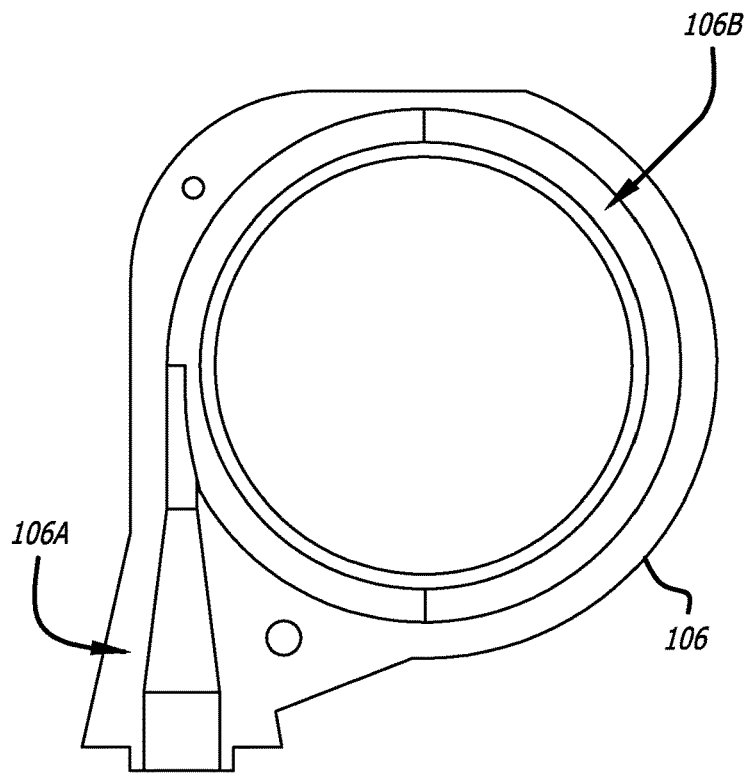
FIG. 4C illustrates a top view of the housing middle of FIG. 4A.

FIGS. 4A-4C illustrate various views of the housing middle 106 which includes a groove 106B disposed around a circumference of the opening of the housing middle 106 which connects to an outlet groove 106A forming a constricted volute shape. Both grooves 106A and 106B cooperate with the raised portion 102A to complete the outlet passage 102B when the housing top 102 is bolted (or alternately welded) to the top surface shown in FIG. 4A. The groove 106B includes a relatively constant width or shape while the outlet groove 106A increases in width towards its end (i.e., towards the exit point of the outlet).

Generally, this volute shape minimizes the risk of thrombus formation by providing a steady "leakage" behind the rotor assembly 105 to prevent stagnation of the flow. As seen best in FIGS. 16, 17A and 17B, this leakage begins in the cylindrical gap between the outer diameter of the rotor assembly 105 and the inner diameter of the housing middle 106, flowing axially to the backside of the rotor assembly 106. Next, the blood flows toward the center of the rotor assembly 105, between the thrust plate 114 and the backside of the rotor assembly 105. Finally, the blood flows forward in the clearance between the bore of the rotor assembly 105 and the outer diameter of the spindle 114D, flowing back over the top of the spindle 114D. Low flow can therefore be achieved with this blood circulation path by generating a pressure gradient that is higher at the periphery of the rotor assembly 105 than at the center of the rotor assembly 105.

Normal operation of a typical centrifugal pump generates a pressure gradient so that the pressure rises as fluid approaches the outlet of the rotor blades. In a typical left ventricle assist device (LVAD) implantation, this pressure would be high enough to ensure good leakage around the rotor, similar to the flow path previously described. In such an arrangement, the static pressure at the periphery of the impeller is less than the pressure at the pump discharge nozzle. This is due to the volute and discharge nozzle being shaped to convert velocity head to static head and improve the hydraulic efficiency of the pump.

However, the design of the present preferred embodiment considers applications that are not configured with a higher pressure head at the outlet of the pump versus the inlet. More specifically, the "working head" of the present preferred embodiment is low and therefore if an efficient, optimized volute and discharge nozzle (i.e., outlet 108) were used, the driving pressure would not be enough to insure sufficient leakage across the leak path.

Accordingly, the present preferred embodiment increases the driving pressure across the leak path by increasing the pressure in the pump housing by throttling the flow with a constricted volute shape, as previously described. The diameter of the torus-shaped volute is so small (e.g., between about 2-5 mm in diameter) that there is significant pressure losses in the volute. These losses in the volute result in a lower pressure at the outlet 108 compared to the pumping chamber inside the pump 100. The resulting higher pressure at the periphery of the rotor assembly 105 provides enough driving pressure (e.g., about 100 mm Hg at a given design point, e.g., 1.3 lpm, 25 mm Hg at flow rates below a given design point, e.g., 0.7 lpm and 200 mm Hg at flow rates above a given design point, e.g., 2 lpm) and leakage flow to minimize the risk of thrombus formation. For example, when the rotor assembly 105 is rotating between about 2500 RPM to 6000 RPM there is an increase of about 50%-100% over the pressure measured at the outlet.

FIGS. 5A-5G show the housing bottom 104 that defines an annular depression or compartment 104A (seen best in FIGS. 5D-5G) which receives the motor assembly 103 described later in this specification. As seen in the Figures, the compartment 104A is sealed (e.g., laser welded) at a bottom of the pump 100 with a bottom cover 115 (seen best in FIG. 16).

Figure 5A:
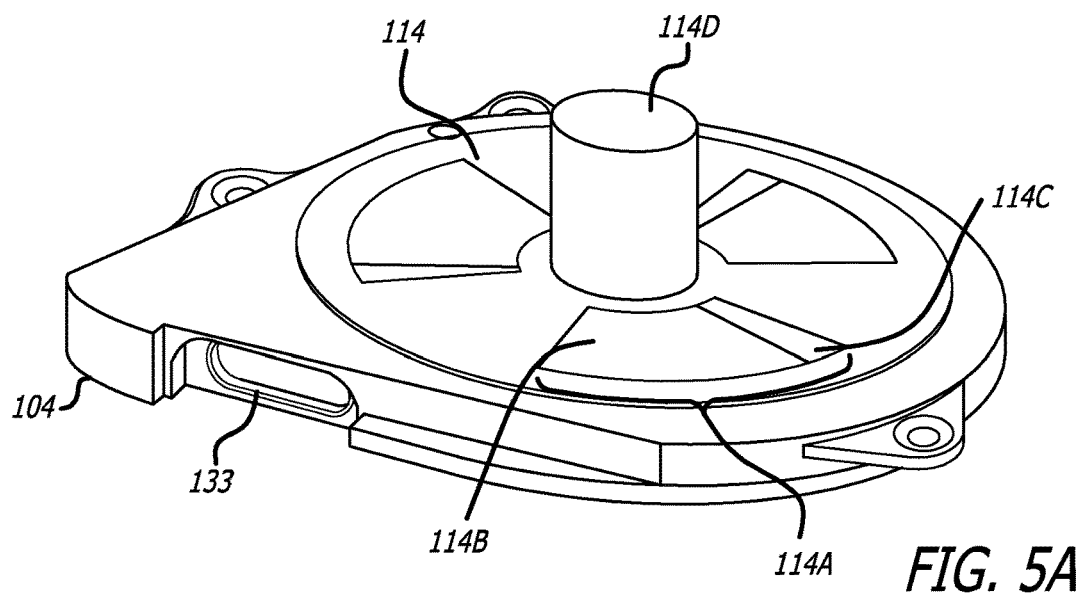
FIG. 5A illustrates a perspective view of a housing bottom according to the present invention.
Figure 5B:
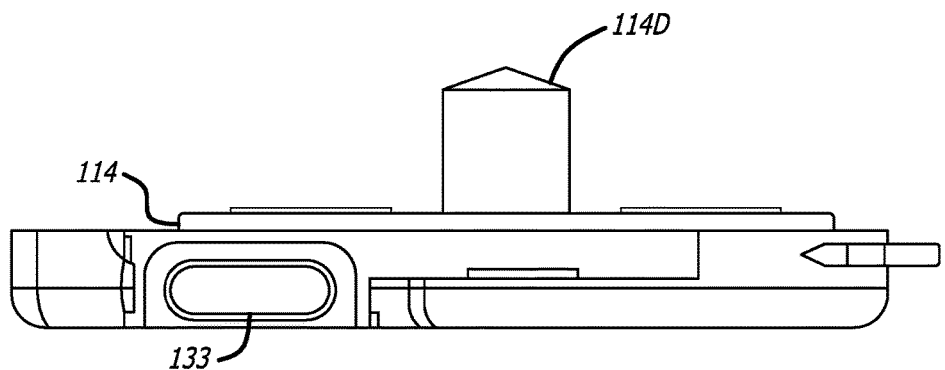
FIG. 5B illustrates a view of the housing bottom of FIG. 5A according to the present invention.
Figure 5C:
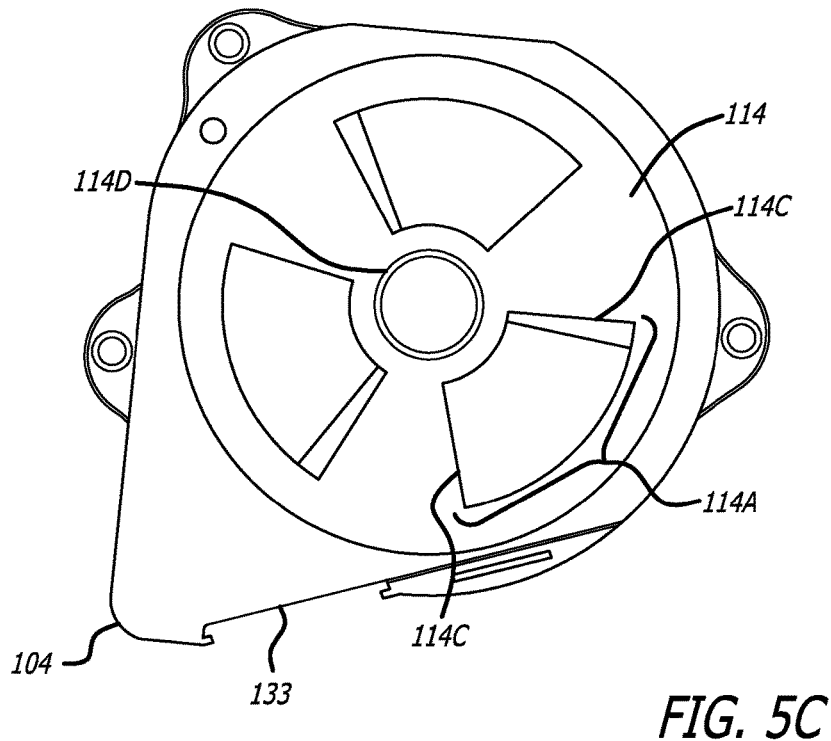
FIG. 5C illustrates a plan view of the housing bottom of FIG. 5A according to the present invention.
Figure 5D:
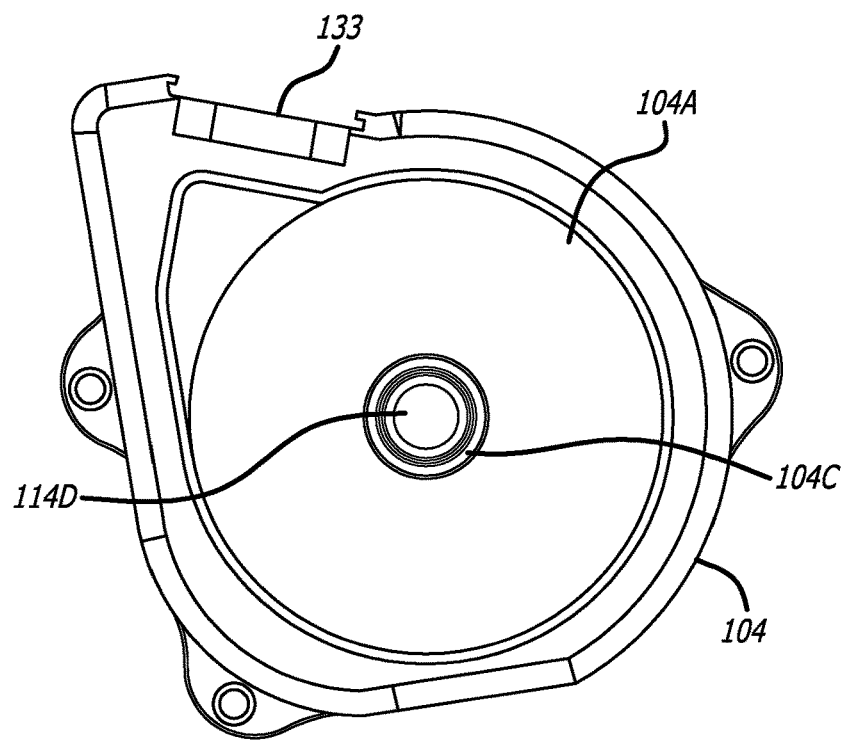
FIG. 5D illustrates a bottom view of the housing bottom of FIG. 5A according to the present invention.
Figure 5E:
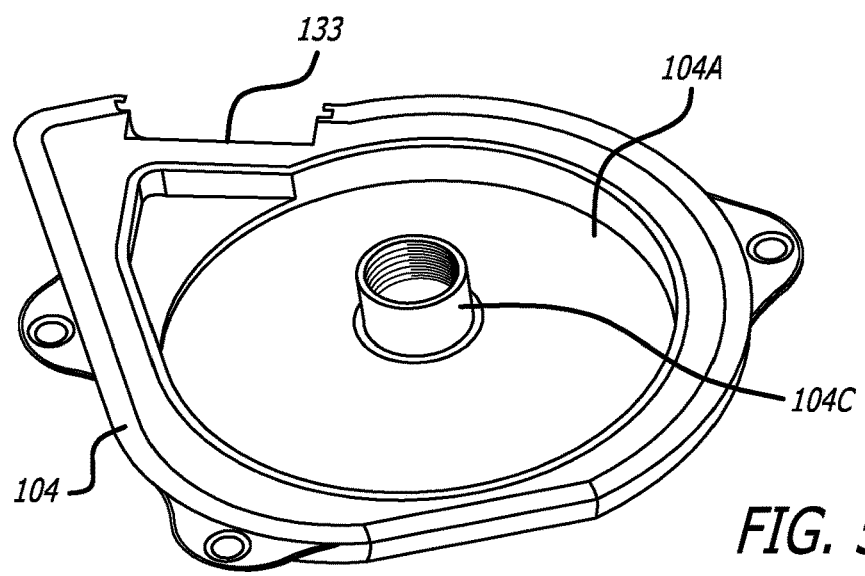
FIG. 5E illustrates a bottom perspective view of the housing bottom of FIG. 5A according to the present invention.
Figure 5F:
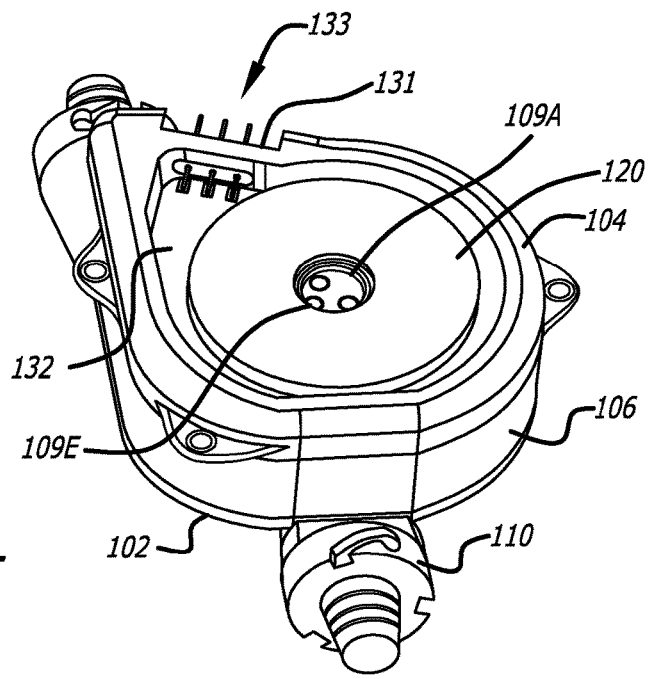
FIG. 5F illustrates a bottom perspective view of a preferred embodiment according to the present invention.
Figure 5G:
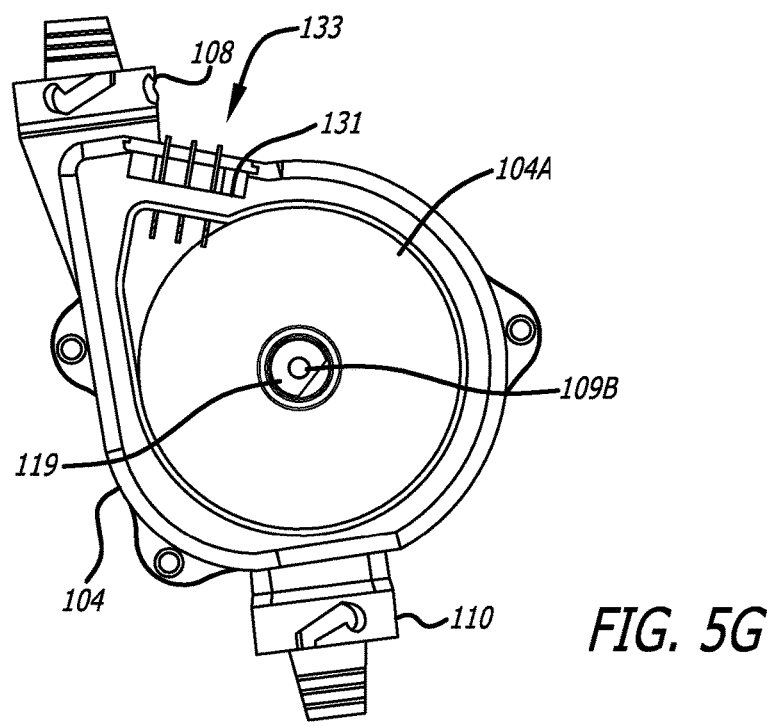
FIG. 5G illustrates a bottom view of the housing bottom according to the present invention.
Figure 5H:
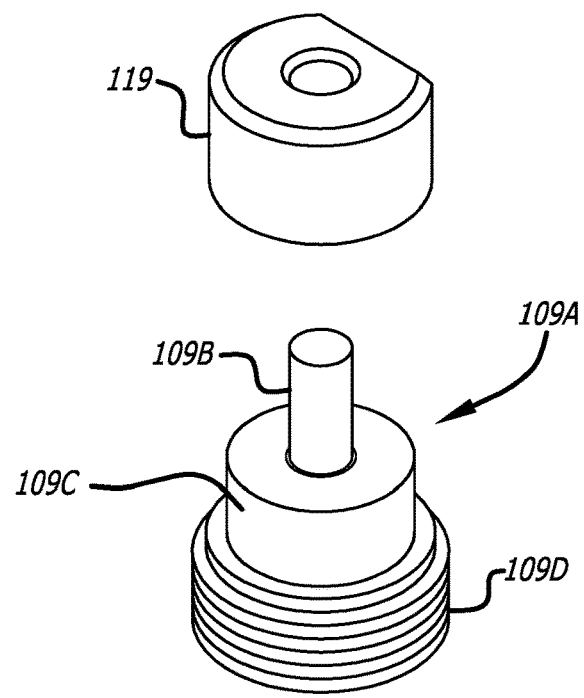
FIG. 5H illustrates a perspective view of a shaft assembly from FIG. 5F.
Figure 5I:
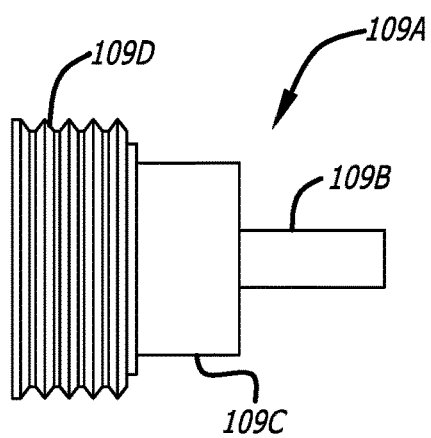
FIG. 5I illustrates a profile view of the shaft assembly from FIG. 5G.
Figure 6A:
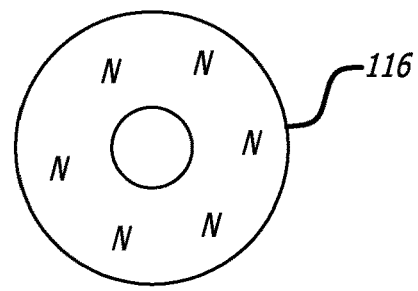
FIG. 6A illustrates a top view of a spindle magnet according to the present invention.
Figure 6B:
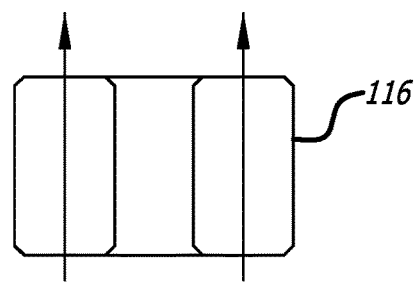
FIG. 6B illustrates a cross-sectional view of the spindle magnet of FIG. 6B.
Figure 6C:
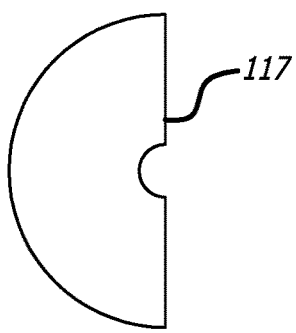
FIG. 6C illustrates a top view of an spindle magnet according to the present invention.
Figure 6D:
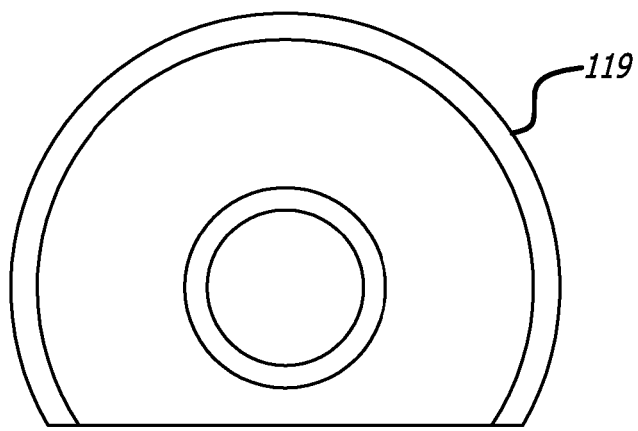
FIG. 6D illustrates a top view of an spindle magnet according to the present invention.
Figure 6E:
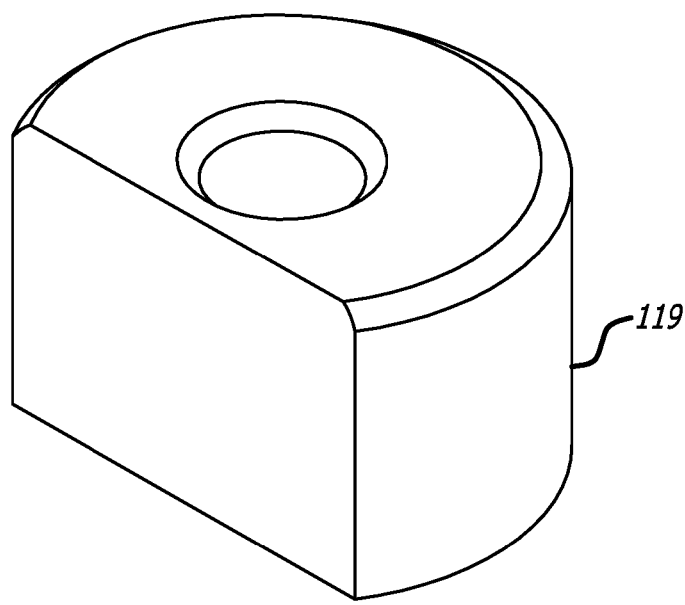
FIG. 6E illustrates a perspective view of an spindle magnet according to the present invention.
Figure 7A:
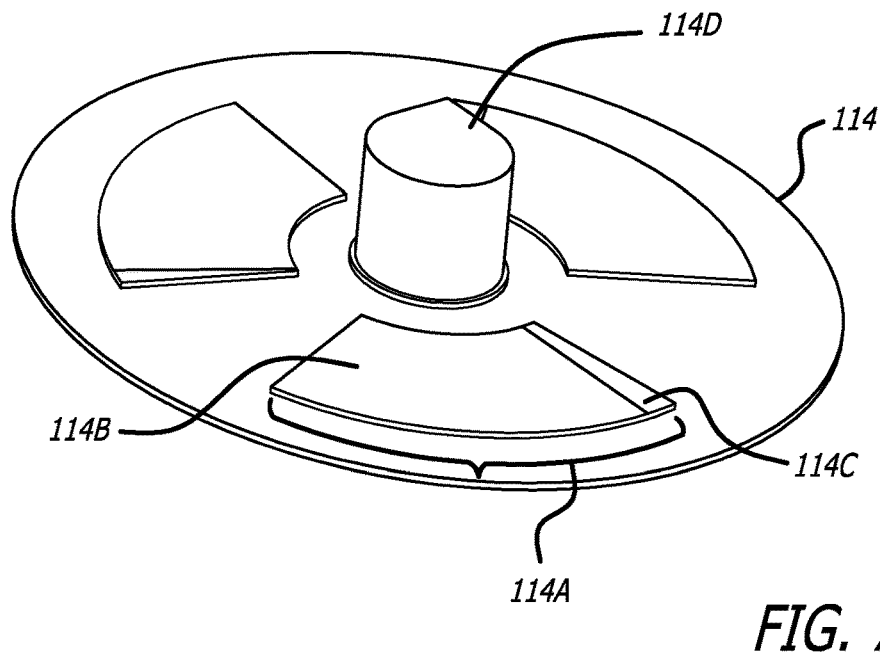
FIG. 7A illustrates a perspective view of a thrust bearing plate according to the present invention.
Figure 7B:
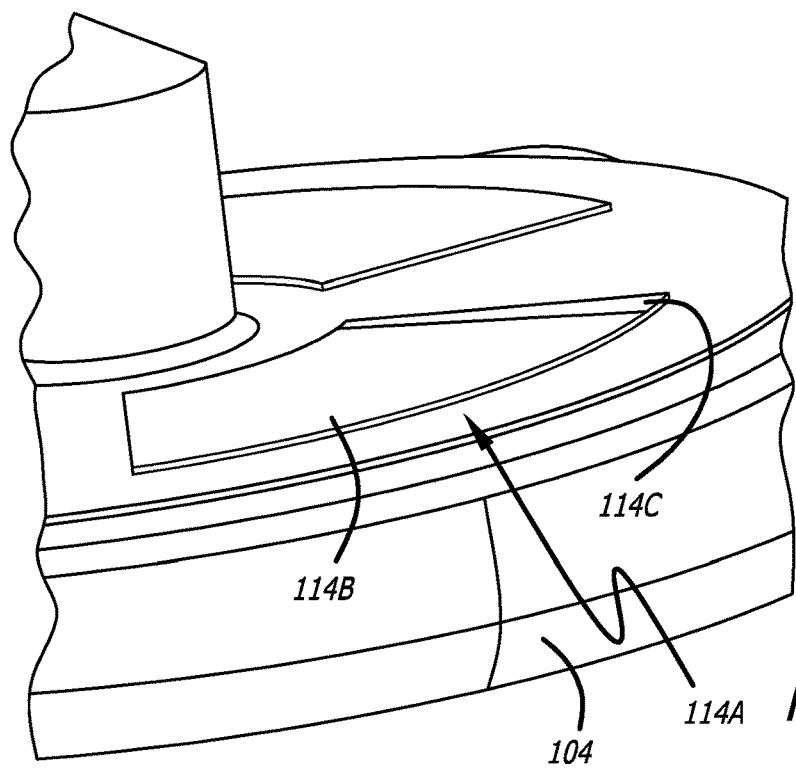
FIG. 7B illustrates a magnified perspective view of the thrust bearing plate of FIG. 7A.
Figure 7C:
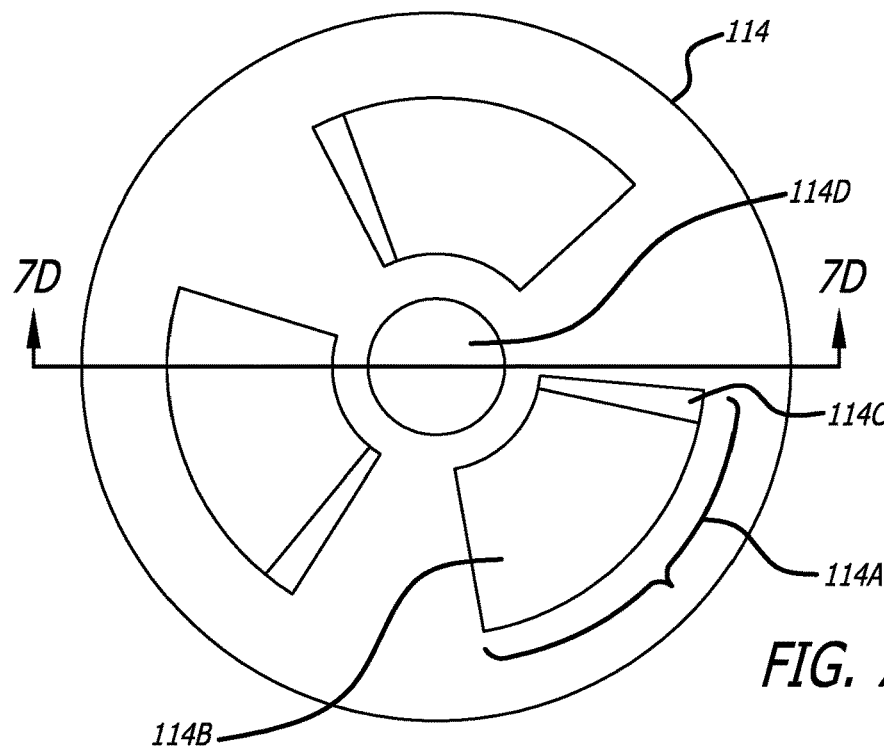
FIG. 7C illustrates a top view of the thrust bearing plate of FIG. 7A.
Figure 7D:
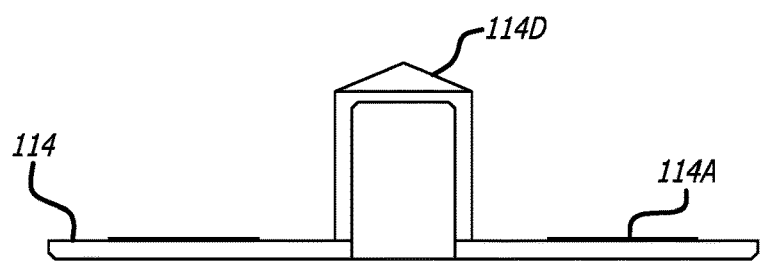
FIG. 7D illustrates a cross-sectional view of the thrust bearing plate of FIG. 7A.

In addition to the motor assembly 103, the compartment 104A also allows access to the interior of spindle 114D of the thrust plate 114 (FIGS. 7A-7D) which contains the spindle magnet 119, seen in FIGS. 5H, 6D and 6E, and the shaft assembly 109A (5H and 5I) that partially make up the axial bearing of the pump. As seen best in FIG. 5H, a center aperture of the spindle magnet 119 slides over a spindle shaft 109B and is supported by a journaled base 109C. A threaded portion 109D of the shaft assembly 109A screws into the threaded center passage 104C so that the spindle magnet 119 is positioned within the interior of the spindle 114D. While this threaded arrangement maintains the position of the shaft assembly 109A, it also allows the user to adjust the axial height of the spindle magnet 119 within the interior of the spindle 114D. In other words, the user can rotate the shaft assembly 109A to axially move the spindle magnet 119 (visually tracking the rotation of the assembly 109A with the marker 109E). Thus, the user can fine tune the axial magnetic bearing as desired to optimize performance of the pump 100.

In an alternate preferred embodiment, not shown, the compartment 104A of the housing bottom 104 may be accessible from a top or inner surface. More specifically, the thrust plate 114 may be nonintegral or removable, preventing access from an outside of the pump 100.

As seen in FIGS. 7A-7D, a top surface of the housing bottom 104 includes an integral thrust plate 114 which includes the previously mentioned spindle 114D containing the spindle magnet 119. The thrust plate 114 has at least three lifts 114A, each being made of an elongated sloping surface 114B and an elevated, shortened, flat surface 114C. In one example, the elongated sloping surface 114B is between about 0.5 degrees and about 3 degrees relative to the top surface of the thrust plate 114. These lifts 114A produce a hydrodynamic bearing when the clearance between the rotor assembly 105 and the lifts 114A of the thrust plate 114 falls below a predetermined threshold. In one embodiment, the predetermined threshold is within a range of about 0.0002 inches to 0.001 inches. Additional examples of hydrodynamic bearings can be seen in U.S. Pat. No. 6,250,880 to Woodard et al., the contents of which are hereby incorporated by reference. In one embodiment, as shown in FIG. 10C, the lifts 114A can be disposed on the rotor assembly 105 instead of the thrust plate 114.

Figure 8:
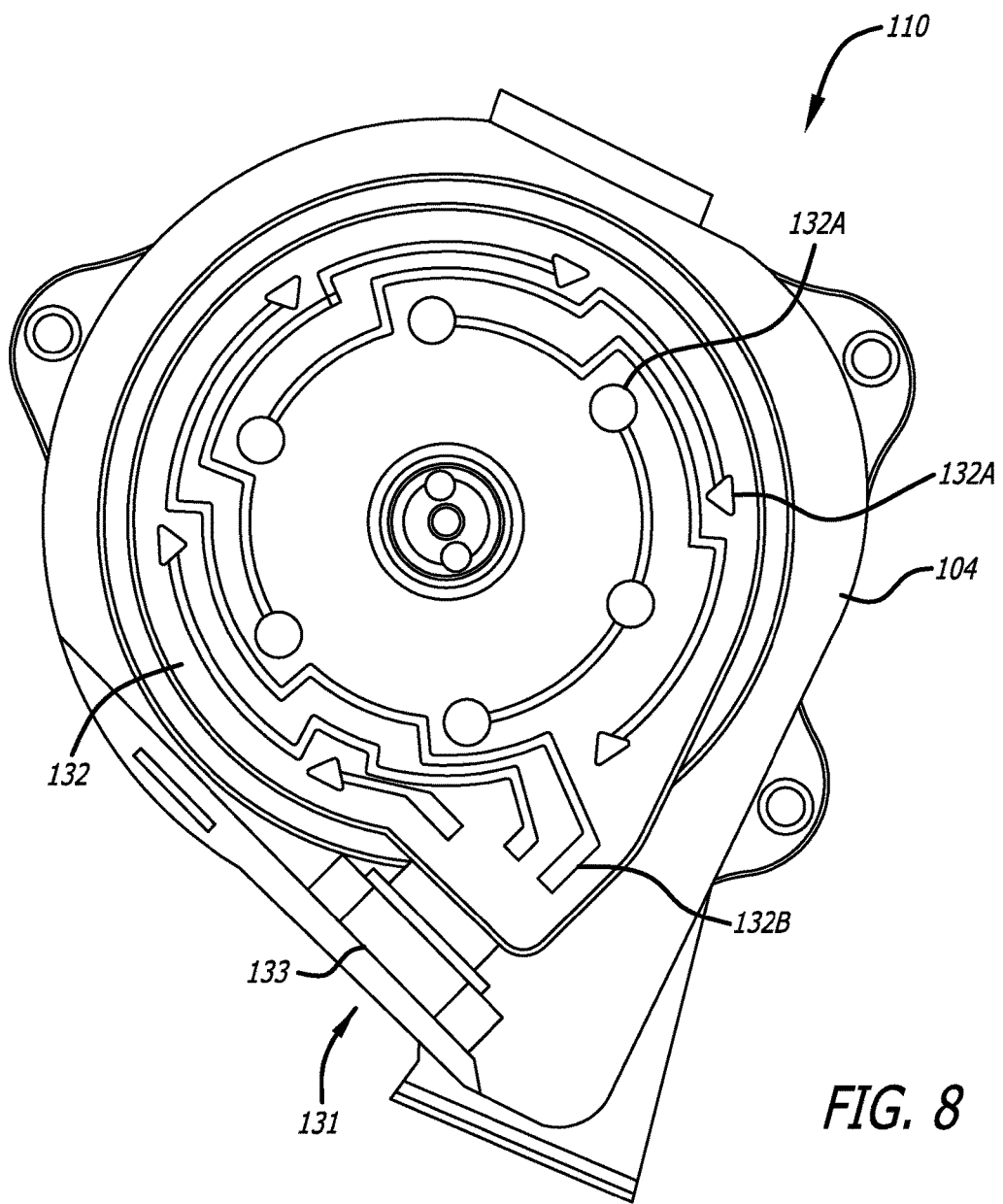
FIG. 8 illustrates a bottom view of a flexible circuit according to the present invention.
Figure 9A:
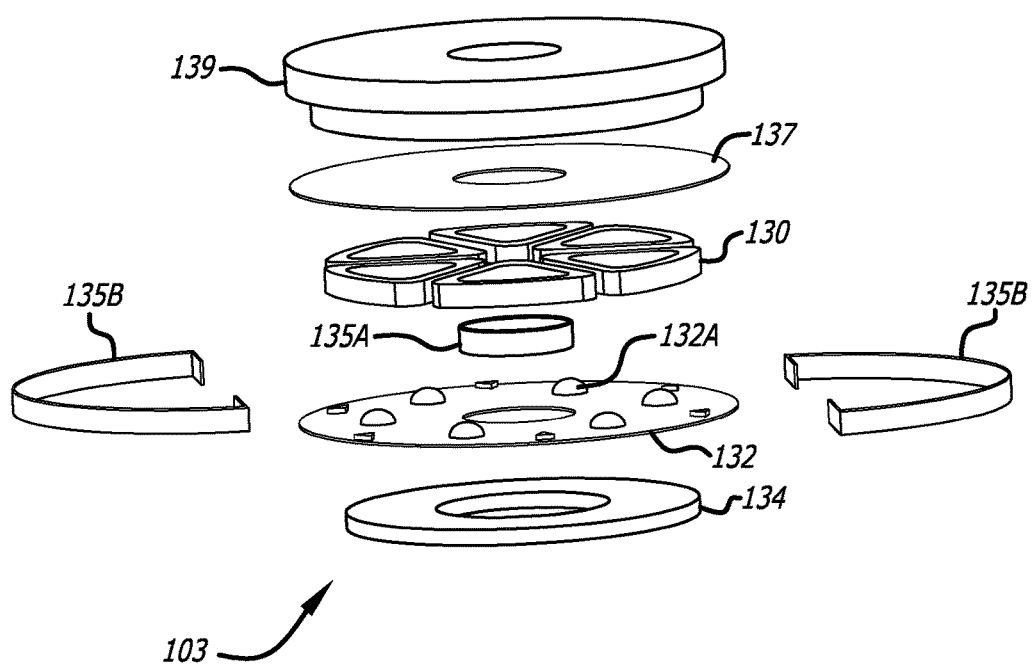
FIG. 9A illustrates a perspective exploded view of a motor assembly according to the present invention.
Figure 9B:
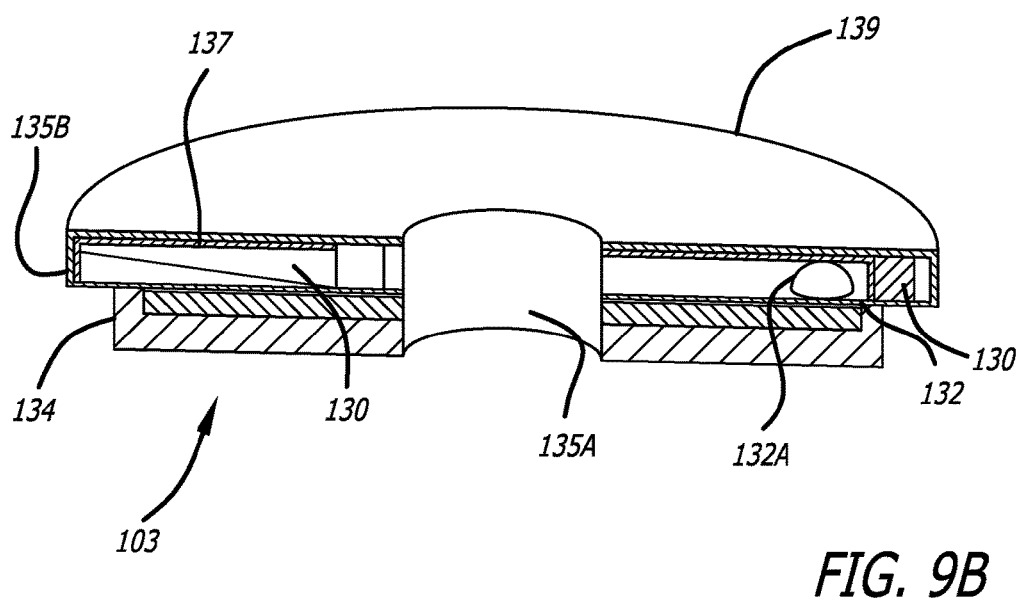
FIG. 9B illustrates a cross sectional view of the motor assembly of FIG. 9A.
Figure 9C:
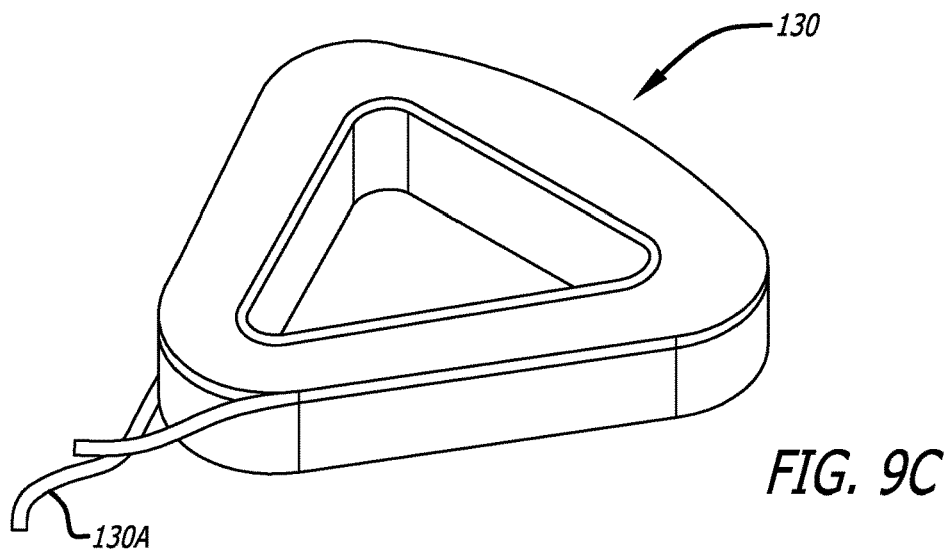
FIG. 9C illustrates a perspective view of a coil according to the present invention.
Figure 9D:
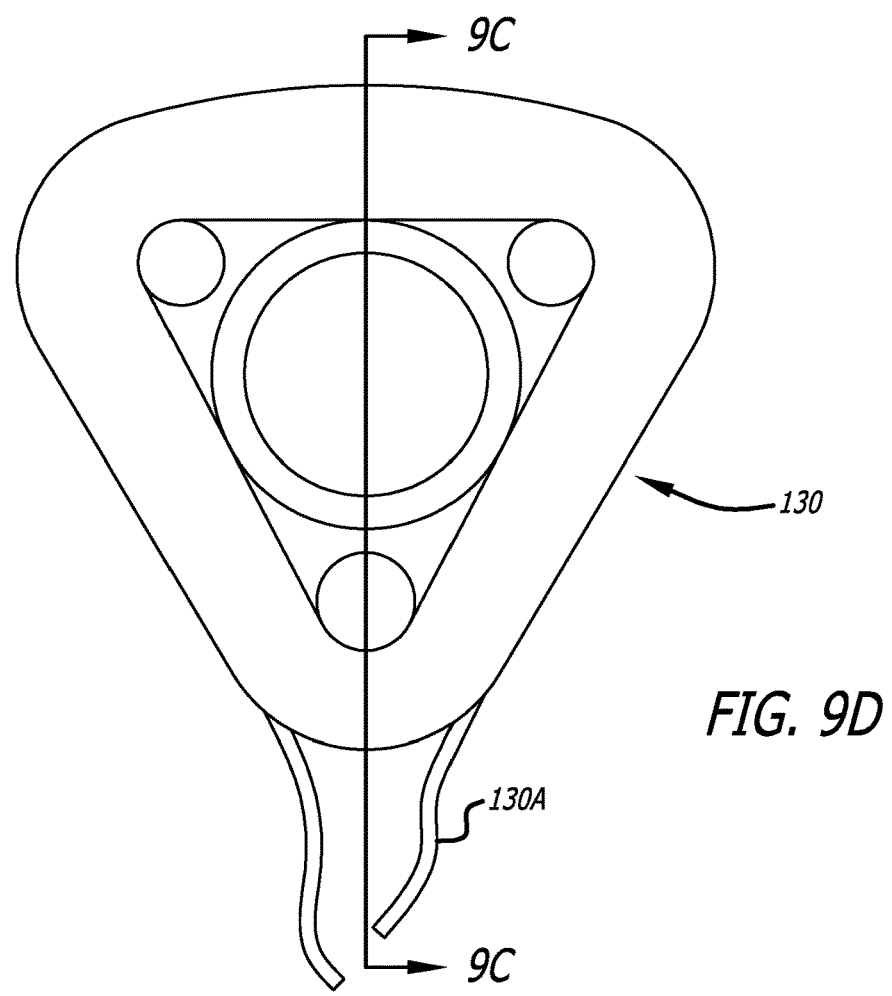
FIG. 9D illustrates a top view of the coil of FIG. 9C.
Figure 9E:
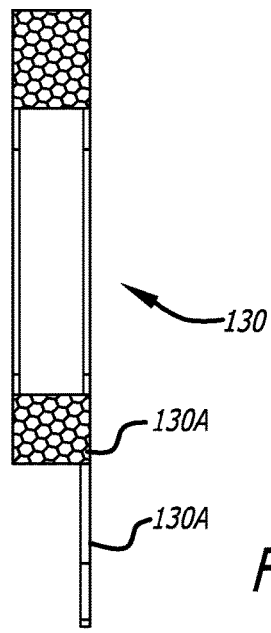
FIG. 9E illustrates a cross-sectional view of the coil of FIG. 9C.

Within the sealed, annular compartment 104A sits the motor assembly 103, as best seen in FIGS. 2, 8, 9A and 9B. The motor assembly 103 generates magnetic fields by conducting electricity through the wire 130A of coils 130, as shown in FIGS. 9C-9E. The wire 130A of each coil 130 is connected to a contact point 132A on flexible circuit 132, as best seen in FIG. 8. The flexible circuit 132 is generally thin and circular in shape, connecting via three contacts 132B to an elongated region of leads 131 that exit the pump 100 fed through a passage 133 within the wall of circular compartment 104A of the housing bottom 104, as best seen in FIG. 2. The end of this outer elongated region of wires 131 then connects to a cable (not shown) and ultimately to a controller (also not shown) which provides the electrical power necessary to generate the desired magnetic fields to drive the rotor assembly 105. It should be understood that the position of the contact points 132A on the flexible circuit 132 may be arranged in a variety of different configurations. For example, the contacts 132A near the circumference of the flexible circuit 132 may be located closer to the center of the circuit 132 to better electrically insulate the contact points 132A.

It should be noted that in an alternate preferred embodiment where the thrust plate 114 is not integral with the housing bottom 104 (e.g., the thrust plate 114 is attached with a bonding agent or epoxy), the top side of coils 130 are covered with a titanium foil which is welded to the housing bottom 104 to provide a hermetic seal between the blood and the motor assembly 103. The thrust plate 114, which may also be composed of titanium, can additionally be welded to the housing bottom 104. In the preferred embodiment where the thrust plate 114 is an integral part of housing bottom 104, the titanium foil is not necessary.

The motor assembly 103 also includes a back iron 134, having a circular shape similar to that of the circular compartment 104A. Preferably the back iron 134 is positioned underneath the flexible circuit 132 to enhance the magnetic fields generated by the coils 130. Once activated, the motor assembly 103 generates magnetic fields that drive the rotation of the rotor assembly 105, positioned above the thrust plate 114.

Additionally, the motor assembly 103 includes outer members 135B, inner member 135A and top member 137 which are preferably composed of a nonconductive material to help electrically insulate the coils 130.

Figure 10A:
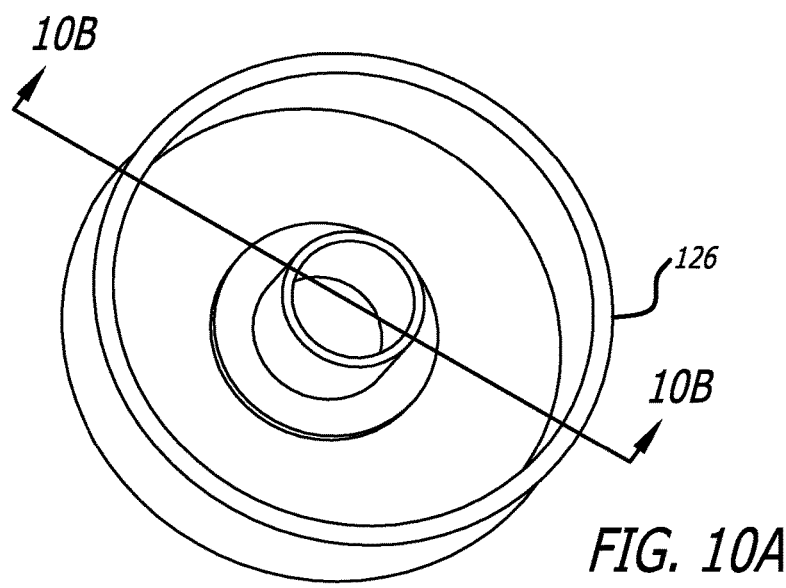
FIG. 10A illustrates a top view of a rotor housing bottom according to the present invention.
Figure 10B:
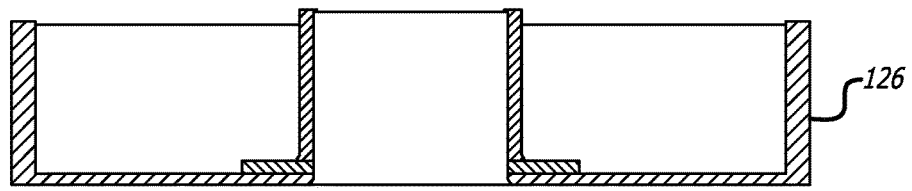
FIG. 10B and FIG. 10C illustrate a cross-sectional view of embodiments of the rotor housing bottom of FIG. 10A.
Figure 10C:
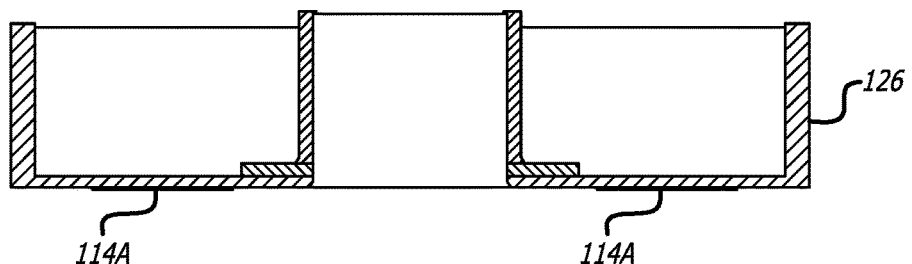
Figure 11A:
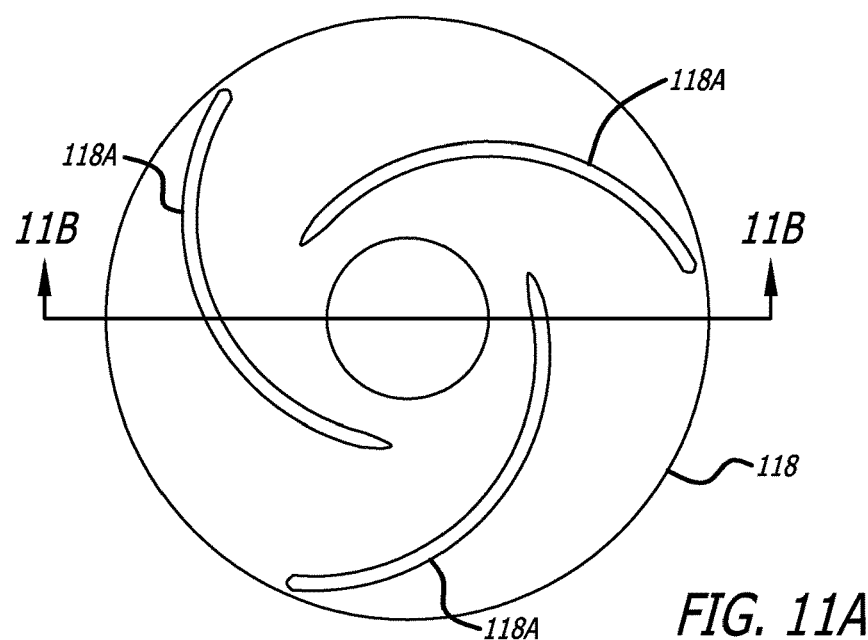
FIG. 11A illustrates a top view of a rotor housing top according to the present invention.
Figure 11B:
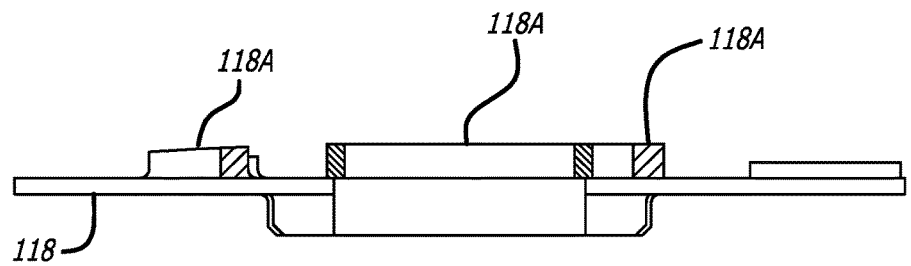
FIG. 11B illustrates a cross-sectional view of the rotor housing top of FIG. 11A.
Figure 11C:
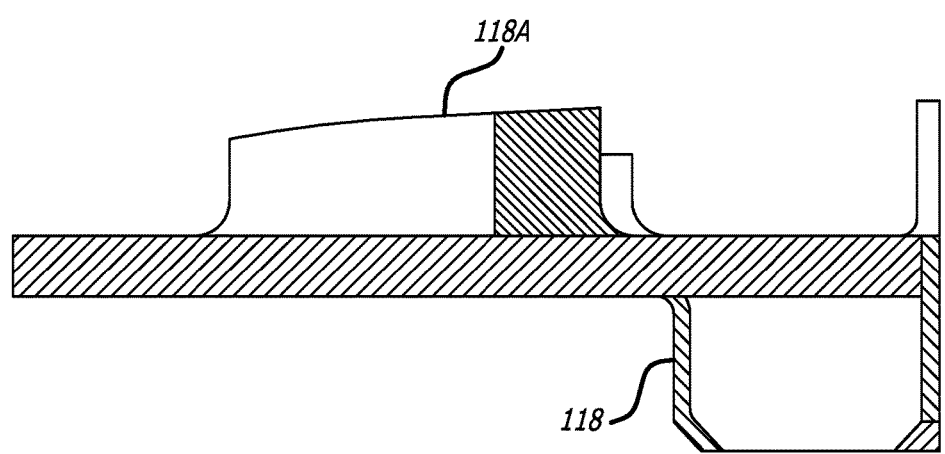
FIG. 11C illustrates a magnified cross-sectional view of the rotor housing top of FIG. 11A.
Figure 11D:
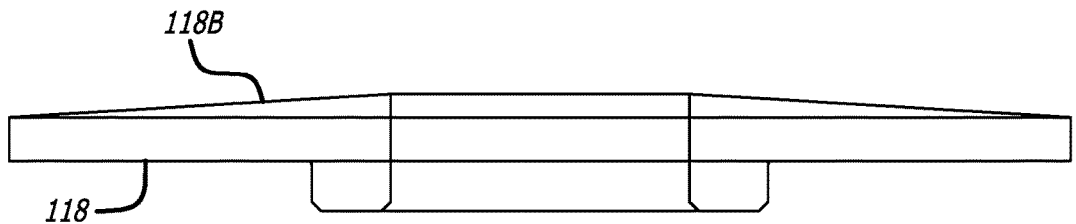
FIG. 11D illustrates a simplified cross-sectional view of the rotor housing top of FIG. 11A.

The outer shape of the rotor assembly 105 is defined by a rotor housing bottom 126, as seen in FIGS. 10A and 10B, and an rotor top 118 as seen in FIGS. 11A-11D. Both rotor top 118 and rotor housing bottom 126 include a center aperture sized to fit around the circumference of spindle 114D of thrust plate 114. The rotor top 118 includes curved impeller blades 118A that drive the incoming blood out of the outlet 108. Preferably, each blade 118A has a height and curve sized to meet desired flow and pressure requirements. Also, the rotor assembly 105 is sized and shaped based on a desired nominal flow and pressure head for a preferred flow range in which the pump will be designed to operate. In one preferred embodiment, the flow range is between about 0.5 and 2.0 liters/minute, and optimally a flow rate of about 1.3 liters/minute. As seen best in FIG. 11D, the top surface 118B of the rotor top 118 includes an overall angled ramp shape. Unlike some prior art designs, the angle of the top surface 118 is relatively shallow, providing an overall thinner profile. For example, the top surface 118B may preferably be angled less than about 10 degrees and more specifically in the range of about 3.80 degrees to 4.00 degrees relative to a horizontal plane.

Figure 13A:
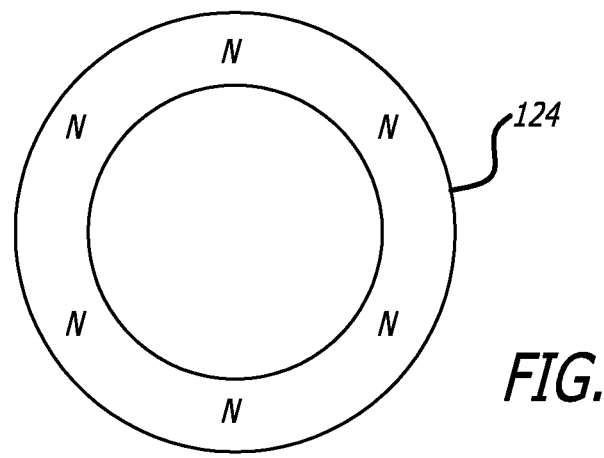
FIG. 13A illustrates a top view of a rotor axial magnet according to the present invention.
Figure 13B:
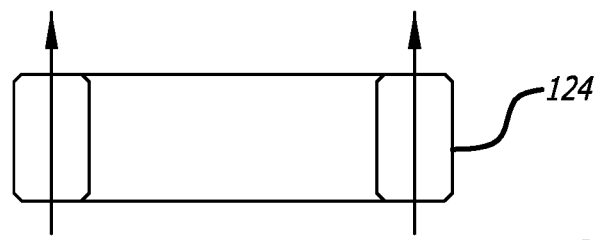
FIG. 13B illustrates a cross-sectional view of the rotor axial magnet of FIG. 13A.
Figure 16:
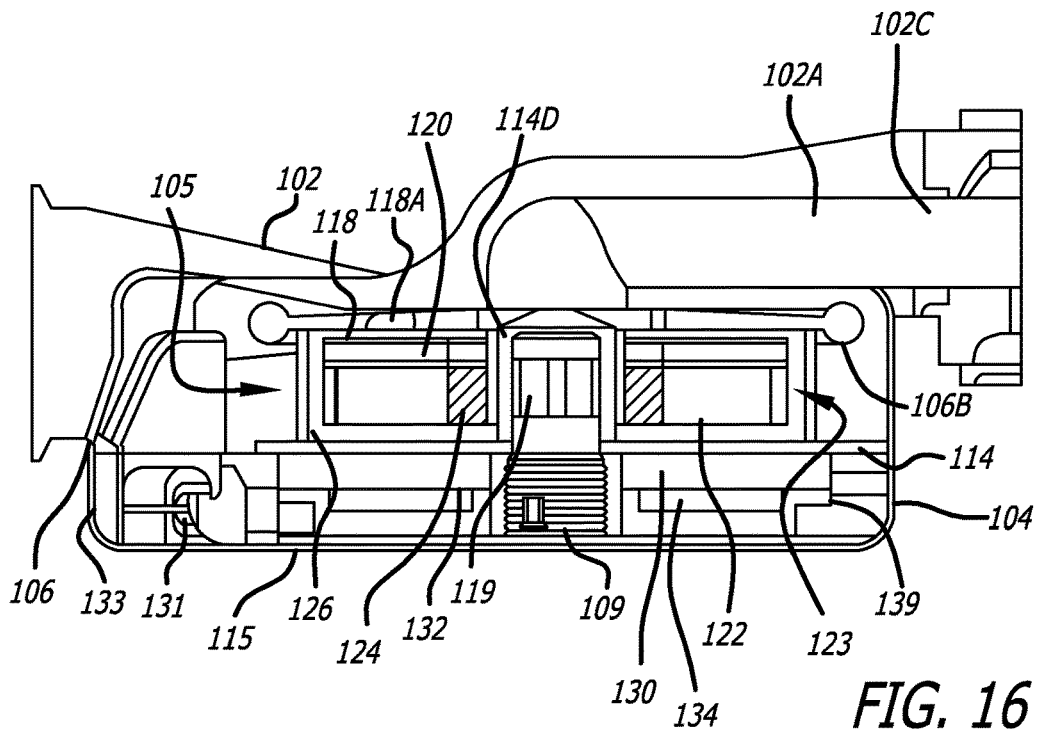
FIG. 16 illustrates a side cross-sectional view of the rotary blood pump of FIG. 1.
Figure 17A:
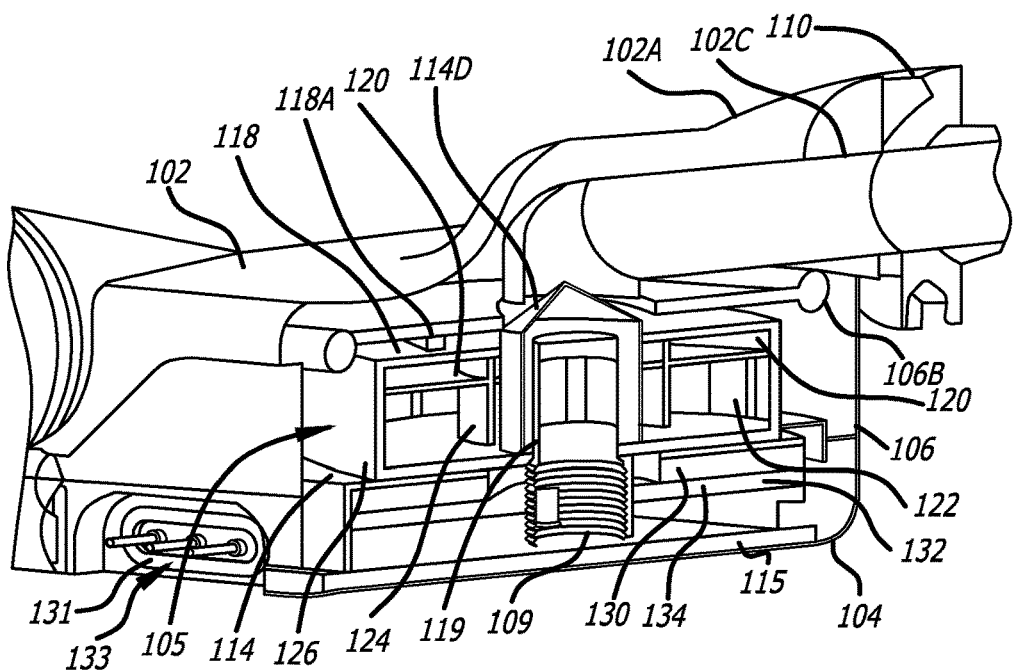
FIG. 17A illustrates a perspective cross-sectional view of the rotary blood pump of FIG. 1.
Figure 17B:
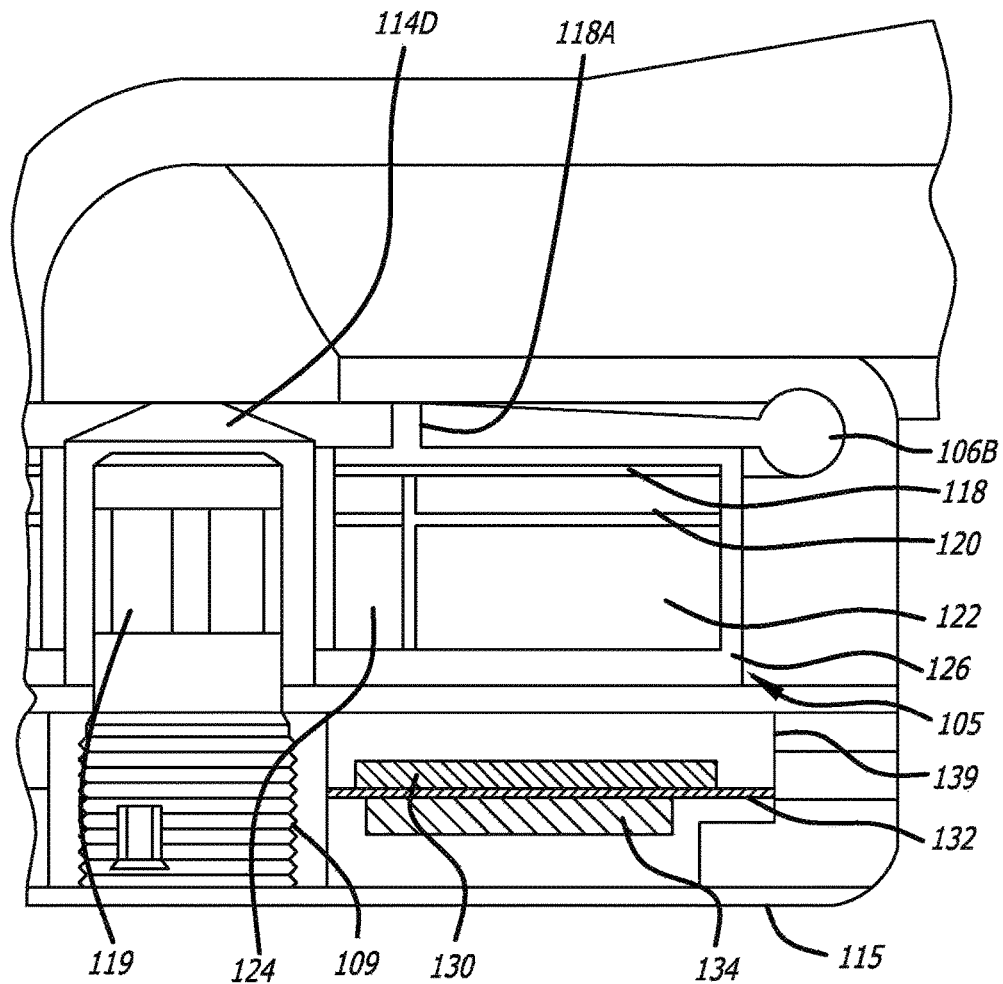
FIG. 17B illustrates a magnified cross-sectional view of the rotary blood pump of FIG. 1.

The rotor assembly 105 contains three main components: the rotor axial magnet assembly 124, a motor rotor magnet 122, and a back iron 120. As best seen in FIGS. 2 and 16, the back iron 120 and the motor rotor magnet 122 have approximately the same diameter, allowing the back iron 120 to sit on top of the motor magnet 122 to enhance the magnetic fields. The rotor axial magnet assembly 124, seen in FIGS. 13A and 13B, is positioned around the inner diameter of the rotor assembly 105 and within the center apertures of the motor magnet 122 and the back iron 120, as best seen in FIG. 16. Preferably, a spacer 123 is also included around the outer perimeter of the inner space within the rotor housing bottom 126 to maintain the position of the motor rotor magnet 122 and back iron 120 within the housing bottom 126.

Figure 12A:
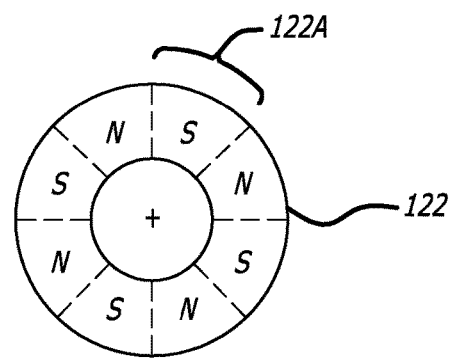
FIG. 12A illustrates a top view of a motor magnet according to the present invention.
Figure 12B:
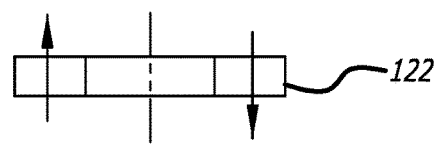
FIG. 12B illustrates a cross-sectional view of the motor magnet of FIG. 12A.

In one preferred embodiment, the motor rotor magnet 122 is composed of a plurality of magnet regions 122A having alternating polarity, as seen in FIGS. 12A and 12B. As the power is applied to the motor assembly 103, the coils 130 generate magnetic fields that drive the motor magnet 122, thus rotating the rotor assembly 105.

The motor rotor magnet 122 is preferably a permanent magnet attracted to the back iron 134 of the motor assembly 103. This attraction tends to pull the rotor assembly 105 towards the thrust plate 114, creating significant axial load on the rotor assembly 105. Previous rotary pump designs, such as those seen in U.S. Pat. Nos. 6,234,772 and 6,250,880, primarily rely on hydrodynamic thrust bearings to overcome this axial loading force. However, since these hydrodynamic bearings utilize a thin layer of blood between a rotor and a thrust plate, the passing blood must support the full force of this axial load. Consequently, blood cells can more easily become damaged due to strong shear forces, creating serious complications such as hemolysis and clotting. Further, the power required to sustain the hydrodynamic bearing increases as the load increases. Thus, highly loaded hydrodynamic bearings can impose a significant power penalty on the pump.

The present invention distributes this axial load force between a hydrodynamic bearing and an axial magnetic bearing as discussed in detail in U.S. application Ser. No. 10/940,419 (previously incorporated by reference). However, it is useful to elaborate on this configuration in the present application.

As previously discussed, the hydrodynamic bearing includes three thrust tapers or lifts on the thrust plate 114 which, due to the relative motion between the bottom surface of the rotor and the thrust tapers 114 creates an upward force on the rotor assembly 105 when in a predetermined proximity to the thrust plate 114. In a preferred embodiment, the cumulative total area of all the lifts 114A is within a range of about 40% to 90% of the total area of the thrust plate 114. It has been determined that three lifts in this configuration provide the necessary hydrodynamic bearing effect necessary for the inventive pump.

As seen in FIGS. 14, 16, 17A and 17B, the axial magnetic bearing includes the rotor axial magnet 124 and the spindle magnet 119. In one preferred embodiment seen in FIG. 14, the rotor axial magnet 124 and the spindle magnet 119 have oppositely aligned magnetic fields in the axial direction. As a result, the magnets 119 and 124 are in a constant state of axial attraction to each other and thereby reduce the axial load on the rotor assembly 105. FIG. 14A illustrates a similar preferred embodiment as FIG. 14 in which the polarity of the magnets 119 and 124 is reversed.

The axial pre-load or bias force produced by the magnets 119 and 124 can be adjusted during assembly of the axial magnetic bearing. Preferably, sufficient positive force should be applied to the rotor toward the rear of the pump in order to stabilize the rotor assembly 105 and prevent undesirable motion at the maximum speed. A minimum force should be applied to achieve this pre-load since excessive force will increase power losses in the hydrodynamic thrust bearings (as discussed elsewhere in this application) and may increase hemolysis.

Preferably, the optimum position of the spindle magnet 119 can be determined empirically during a functional test with a blood analog in a mock circulatory loop. The maximum speed is determined by characterizing the hydraulic performance of a plurality of pumps. Once the maximum speed is established, each pump of the plurality of pumps is adjusted to a flow of 2.0 lpm and a pressure of 105 mm Hg and the position of the axial magnet 119 adjusted until instability of the rotor assembly 105 is detected (e.g., detected by listening to the pump housing assembly 101 for a change in the sound produced). When this instability threshold is detected, the shaft assembly 109A can be rotated (i.e., moved toward the housing bottom 104) beneath this threshold. Thus, the spindle magnet 119 may ultimately be positioned at one of many different heights relative to the rotor axial magnet 124.

Figure 15A:
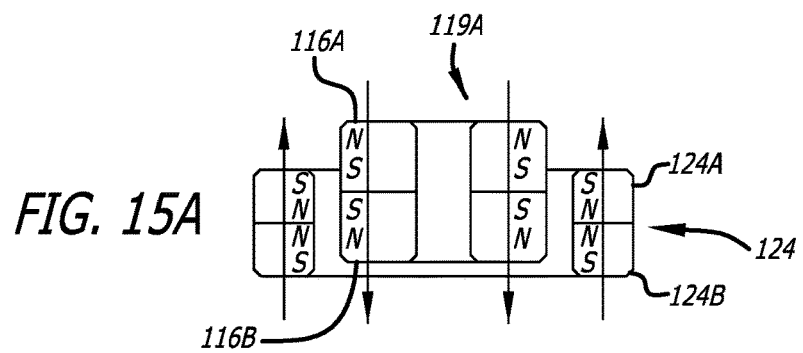
FIG. 15A illustrates a cross-sectional view of a magnetic axial bearing according to the present invention.

FIG. 15A illustrates another preferred embodiment of the axial magnetic bearing in which each of the magnets 119 and 124 are composed of two distinct magnetic regions, positioned to axially align one pole towards another like pole. For example, the top magnetic region 124A of the rotor axial magnet 124 is positioned so that its north pole is pointing downward towards the north pole of the bottom magnetic region 124B. Similarly, the top magnetic region 119A of the spindle magnet 119 is oriented so that its south pole is pointing downwards towards the south pole of the bottom magnetic region 119B. In this respect, the axial magnetic bearing reduces axial load by creating an attractive force between the centers (i.e. like poles) of the rotor axial magnet 124 and the spindle magnet 119 and a repulsive force between the ends of one magnet and the center of the other. For example, the outer south poles of rotor axial magnet 124 produce a repulsive force on the inner south poles of the spindle magnet 119. In this respect, both attractive and repulsive forces are created between the magnets 119 and 124, thereby countering at least a portion of the axial load otherwise imposed on the rotor assembly 105.

Figure 15B:
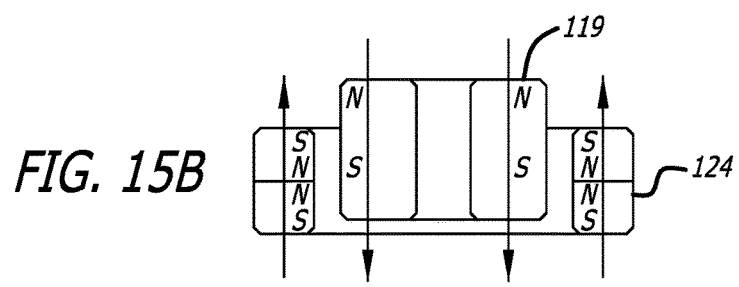
FIG. 15B illustrates a cross-sectional view of a magnetic axial bearing according to a second embodiment of the present invention.
Figure 15C:
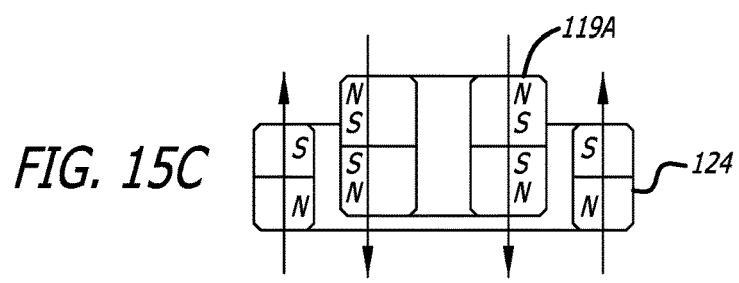
FIG. 15C illustrates a cross-sectional view of a magnetic axial bearing according to a third embodiment of the present invention.

In another preferred embodiment, the magnets 119 and 124 can be composed of a plurality of different combinations of regions. For example, one magnet 119 may have a single N-S region whereas the other magnet 124 has an S-N region on top and an N-S region below it as depicted in FIG. 15B. Similarly, one magnet 119 could have an N-S region on top and an S-N region below whereas the other magnet 124 has a single S-N region as depicted in FIG. 15C.

Figure 14:
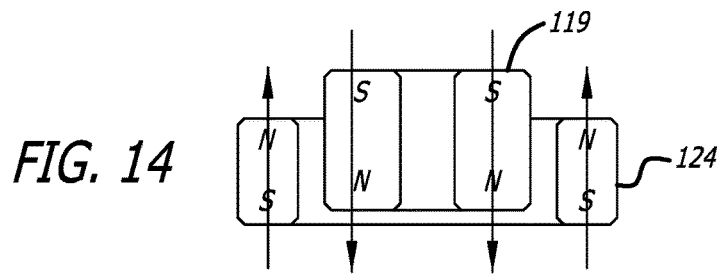
FIG. 14 illustrates a cross-sectional view of a magnetic axial bearing according to the present invention.
Figure 14A:
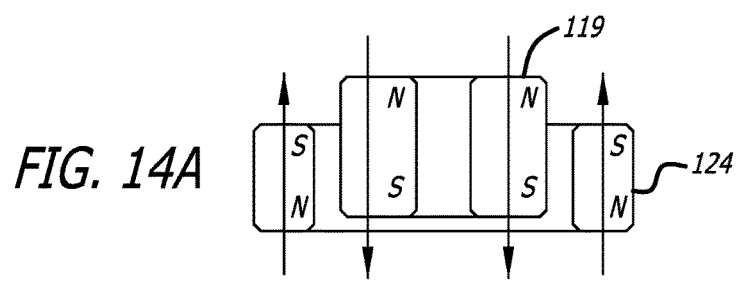
FIG. 14A illustrates a cross-sectional view of a magnetic axial bearing according to the present invention.

The force generated by the axial magnetic bearing in either of the embodiments shown in FIGS. 14 and 15A-15C can be adjusted by replacing the magnets 119 and 124 with higher or lower strength magnets, or simply by adjusting the height of spindle magnet 119 within the pump 100 by adjusting the threaded shaft 109 positioned through center passage 104C of housing bottom 104. The spindle magnet 119 can be positioned at a higher elevation relative to the rotor axial magnet 124 as shown in FIGS. 14 and 15A so as to maximize the upwardly directed axial force on the rotor assembly 105 or a lower elevation to minimize any upwardly directed axial force on the rotor assembly 105.

In yet further embodiments of the invention, the rotor axial magnet 124 could be a permanent magnet whereas the spindle magnet 119 could be a ferromagnetic material, or vice versa. Similarly, the spindle magnet 119 and the axial magnet 124 could be comprised of a two separate regions, one being a made of a permanent magnet material and the other a ferromagnetic material. Of course the polarity of the magnetic materials in any of these embodiments would conform to one of the embodiments discussed above in order to provide the axial bearing load as discussed in connection with the invention.

It should be noted that further embodiments of the magnetic axial bearing are possible according to the present invention. For example, the rotor axial magnets 124 could be disposed near the outer circumference of the rotor assembly 105 while the spindle magnet 119 could be embedded within the sidewall of the housing middle 106. In this respect, the different position of the magnets may also produce an axial force to compensate for downward preloading of the rotor assembly 105.

As best seen in FIG. 16, blood enters the pump 100 through inlet passage 102C and is disbursed by the impeller blades 118A over the top of the rotor and either into the volute and driven out of the outlet 108 on the side of the pump 100 or around the outside of the rotor assembly under the rotor assembly (supplying the fluid for the hydrodynamic thrust bearing) and then up the gap between the spindle and the rotor assembly 105 supplying the fluid for the journal bearing.

In some instances there may exist a radial bias exerted on the rotor assembly 105 due to the movement of the blood flow through the pump 100. For example, as the blood is forced to exit the pump 100, an outlet pressure at the outlet arises that can cause the aforesaid bias on the rotor assembly 105. In one preferred embodiment seen in FIGS. 5G, 6C, 6D, 6E and 18B, compensation of the radial bias can be achieved through the use of a radially asymmetrical or noncircular spindle magnet 119 in the axial magnetic bearing to create an asymmetrical magnetic field. For example, the spindle magnet can have an asymmetrical or noncircular cross sectional shape, such as the "D" shape of spindle magnet 119 in FIGS. 6D and 6E and spindle magnet 117 shown in FIG. 6C. This shape can be positioned in such a way as to increase the magnetic force in a predetermined direction and magnitude, opposite to the bias force. Specifically, the curved areas of spindle magnet 119 produce a greater magnetic field relative to the flat side. In other words, the spindle magnet 119 is shaped such that the center of its mass is offset from an axis of rotation of the axial magnetic bearing and therefore is also offset relative to the rotor axial magnet 124 of the rotor assembly 105. Thus, the area of the spindle magnet 119 having the greater magnetic field can be oriented opposite the direction of the bias force (bias force pointing into flat side of magnet 119), producing more force on the rotor axial magnet 124 in that direction and thereby reducing or substantially eliminating the effects of the bias force on the rotor assembly.

In another preferred embodiment, this bias is compensated with surface features such as sloping surfaces, tapers, pads, or other surface geometry changes along the thrust plate 114, the inner circumferential surface of the housing middle 106, or both. By placing these features unevenly, for example on one side of the housing middle 106, a hydrodynamic bearing is created on one side of the pump 100, creating a biasing force in a radial direction. With proper positioning of these radial hydrodynamic bearings, the outlet 108 bias force can be substantially reduced.

Figure 18A:
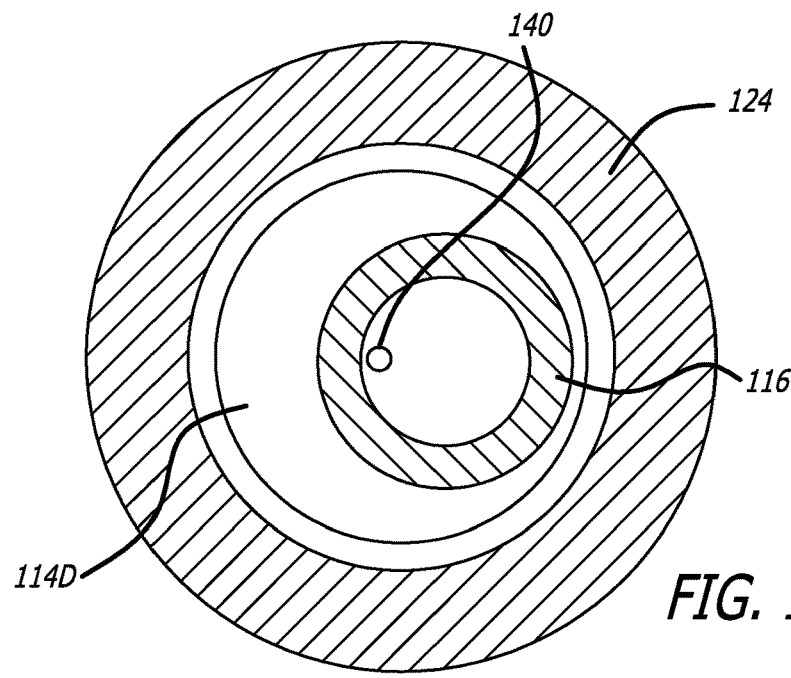
FIG. 18A illustrates a top cross-sectional view of a magnetic axial bearing according to the present invention.
Figure 18B:
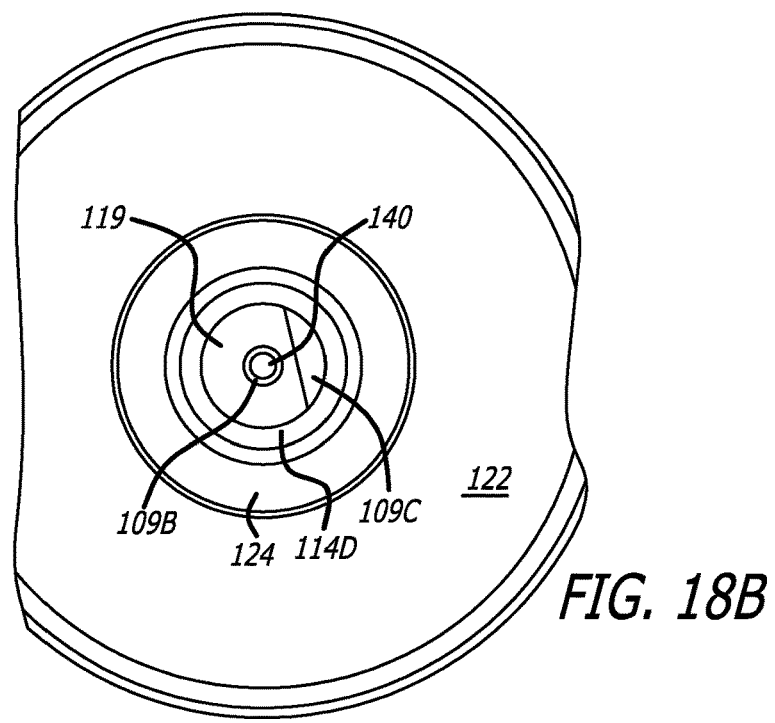
FIG. 18B illustrates a top cross-sectional view of a preferred embodiment of a magnetic axial bearing according to the present invention.

In another preferred embodiment, this radial bias is compensated for by offsetting the spindle magnet 116 from the center of the spindle 114D and rotor axial magnet 124. For example, FIG. 18A illustrates the spindle magnet 116 positioned to one side of the center 140 of the spindle 114D. Depending on the configuration of the magnets 116 and 124, the offset spindle magnet 116 produces a net radial force as the rotor assembly 105 rotates. Thus, by creating a radial force with an equal and opposite force, the radial bias introduced by the blood exiting the pump can be counteracted.

Another aspect of the present invention is the interaction of the hydrostatic pressures of the pump, the axial loads between the motor rotor magnet 122, the stator back iron 120, and the axial magnet 124 and the hydrodynamic bearing created with thrust plate 114. This is described in greater detail below.

During operation of the pump 100, the curved impeller blades 118A of the rotor top 118 generate hydrostatic pressure, most of which is used to create useful flow through the outlet 108. In all centrifugal pumps a hydrostatic pressure is applied to all wetted surfaces of the rotor and housing. The sum of this hydrostatic pressure produces a net force on the rotor which must be carried by bearings. These forces can be difficult to measure; however, they can more easily be predicted with computational fluid dynamic analysis as known in the art. Computational fluid dynamics (CFD) is a finite element program that allows modeling and prediction of the performance of a pump. The results of this analysis can then be used to determine such parameters that can be expected from a particular design, such as the hydraulic performance, efficiency, resulting forces, and shear.

One commercial CFD program, ANSYS CFX-5, was used to create a CFD model of the pump 100 according to the present invention. A periodic model of the complete rotor assembly 105 with the backside, housing clearances and hydrodynamic bearings was used to evaluate forces acting on the rotor assembly 105 and leakage behind the rotor assembly 105.

A laminar model was used since the calculated Reynolds number is a maximum of 236, which is well within the laminar range and well below the transition range of 2,000. The formula for the Reynolds number is:

$$R = \rho V D / \mu$$

In this formula, $\rho$ is density (1.0 kg/l), V is velocity (6.5 m/s), D is clearance (0.0127 cm) and $\mu$ is viscosity (3.5 cps).

Figure 19:
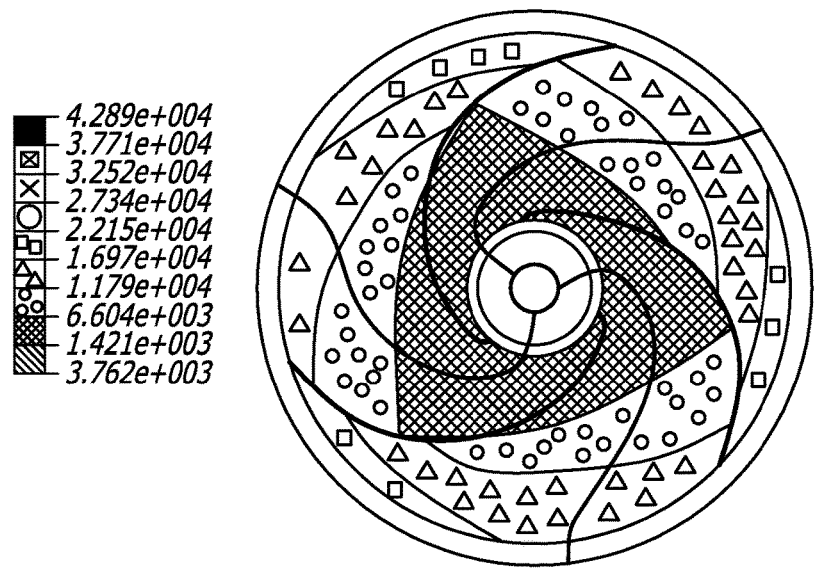
FIG. 19 illustrates a contour plot of the hydrostatic pressure acting on the rotor assembly according to the present invention.

FIG. 19 shows a contour illustration of the hydrostatic pressure acting on the rotor assembly 105. The pressure units are in pascals (1 pascal=0.0075 mm Hg). The function calculator of the software indicates that the area average pressure on the hub of the rotor assembly 105 is 9754 pascals or 73.15 mm Hg (1.415 psi). The annular area of the rotor assembly is 1.041 square inches, indicating that the net hydrostatic axial force acting on the hub is 1.472 pounds directed toward the rear or the bottom of the pump.

Figure 20:
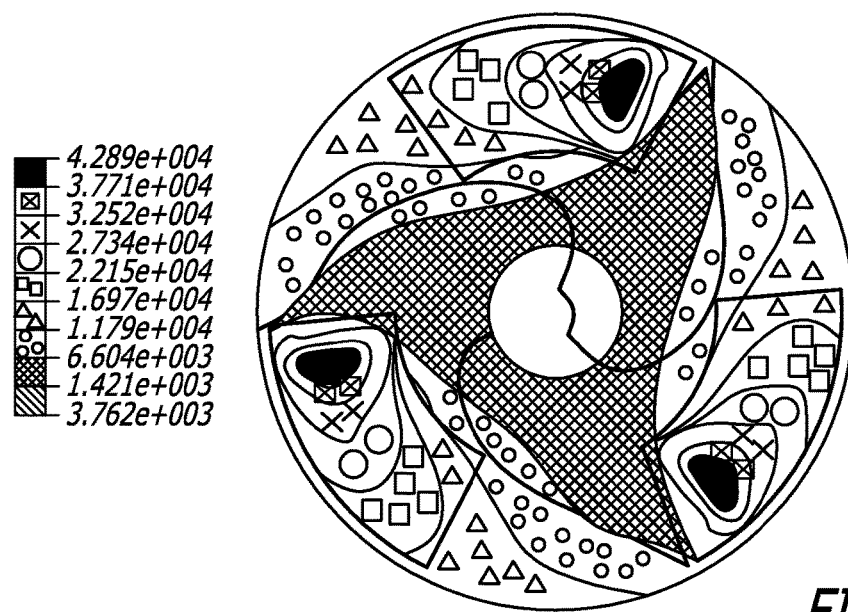
FIG. 20 illustrates a contour plot of the hydrostatic and hydrodynamic pressure acting on the bottom of the rotor assembly according to the present invention.

FIG. 20 illustrates a contour plot of the hydrostatic and hydrodynamic pressure acting on the bottom of the rotor assembly 105, i.e. the rotor housing bottom 126. The outline of the three lifts 114A on the thrust plate 114 can be seen in FIG. 20, as the different pressure regions produced by these bearings. The function calculator of the software indicates that the hydrostatic pressure outside of the region of three lifts 114A is 8395.72 pascals or 62.97 mm Hg or 1.219 psi. The area on the rotor housing bottom 126 is also 1.041 square inches, making the resulting hydrostatic force 1.27 pounds in a direction away from the rear of the pump.

In this respect, the CFD calculations show that the net axial hydrodynamic/hydrostatic force acting on the rotor assembly 105 (i.e. the difference between the force acting on the top of the rotor assembly 105 and the bottom of rotor assembly 105) is 0.202 pounds in a direction towards the rear of the pump. This net axial hydrodynamic/hydrostatic force also combines with the force resulting from the action of the motor magnets 122 and the back iron 134. A typical attractive force for the motor magnets 122 and the back iron 134 would be about 1.1 pounds. Hence, the hydrodynamic bearing formed by the lifts 114A must compensate for a combination of the net hydrodynamic/hydrostatic force (0.202 pounds) and the motor magnet 122 and back iron 134 attractive force (1.1 pounds) for a total axial force of at least 1.302 pounds. In other words, the hydrodynamic bearing produces an amount of force adequate to compensate for both of these forces, thus maintaining the overall position of the rotor assembly 105 during normal operation with minimal to no physical contact with the housing assembly 101.

In conclusion, the operation of the pump is described. In operation, the blood pump 100 is connected to a circulatory system of a patient by the inlet 110 and the outlet 108. The user activates the blood pump 100 by actuating the blood pump controller. The controller delivers the appropriate electrical current to the flexible circuit 132, which then distributes this current to the coils 130. The current traveling through the wire 130A of the coils 130 creates a magnetic field that interacts with the motor magnet 122, driving the rotor assembly 105 to rotate. The magnetic fields of the spindle magnet 119 and the rotor axial magnet 124 interact to create a magnetic axial bearing to help maintain the axial position of the rotor assembly 105 during rotation. As the rotor assembly 105 spins, additional axial force is imparted to the rotor assembly by the hydrodynamic thrust bearing created by the lifts 114A on the thrust plate 114.

As the rotor assembly 105 rotates, the impeller blades 118A on the rotor housing top 118 drive blood from the inlet 110 and inlet passage 102C and out through the outlet 108. In this respect, the rotating rotor assembly 105 drives the patient's blood through the pump 100, assisting in blood circulation.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A method of pumping blood comprising:
   providing a pump housing defining a pump chamber having an inlet and an outlet and a rotor rotatably disposed in said pump chamber;
   spinning said rotor
   generating a hydrodynamic bearing between said pump housing and said rotor using a plurality of a plurality of lifts positioned between said pump housing and said rotor; each of said plurality of lifts being elongated and sloped at an angle relative to a pump chamber surface such that each of said plurality of lifts includes a first planar surface extending at an angle relative to a pump chamber surface and a second planar surface, connected to said first surface, extending substantially parallel to said pump chamber surface; and,
   supporting said rotor with a passive axial magnetic bearing comprised of a pump housing magnet and a corresponding rotor magnet wherein magnetic fields of said pump housing magnet and said corresponding rotor magnet are oppositely aligned in the axial direction;
   said hydrodynamic bearing and said passive axial magnetic bearing cooperating with each other so as to enhance axial stability to said rotor during rotation of said rotor.

2. The method of pumping blood according to claim 1, wherein, said first surface is angled from said pump chamber surface between about 0.5 degrees and about 3 degrees.

3. The method of pumping blood according claim 1, wherein said each of said plurality of lifts is disposed on said rotor.

4. The method of pumping blood according to claim 1, wherein each of said plurality of lifts is disposed on said pump chamber surface.

5. The method of pumping blood according to claim 4, wherein each of said plurality of lifts is formed integrally on said pump chamber surface.

6. The method of pumping blood according to claim 1, wherein said plurality of lifts is comprised of at least three lifts.

7. The method of pumping blood according to claim 1, wherein said plurality of lifts constitutes a cumulative total area within a range of about 40% to 90% of said pump chamber surface area.

8. The method of pumping blood according to claim 1, wherein the plurality of lifts are sized to produce an amount of force adequate to compensate for the sum of the net hydrodynamic/hydrostatic forces of said pump plus an attractive force between a motor magnet and back iron of said pump.

9. The method of pumping blood according to claim 1, wherein said plurality of lifts are sized and shaped to produce a hydrodynamic bearing when a clearance between said pump housing and said rotor is within a range of about 0.0002 inches to 0.001 inches.

10. The method of pumping blood according to claim 8, wherein said compensatory force produced by said plurality of lifts equals at least around 1.302 pounds.

11. A method of pumping blood comprising:
    providing a housing assembly defining an interior pump surface and a rotor rotatably disposed in said housing assembly;
    spinning said rotor;
    forming a hydrodynamic bearing using a plurality of lifts positioned between said housing assembly and said rotor; each of said plurality of lifts comprised of an elongated sloping surface such that each of said plurality of lifts includes a first planar surface extending at an angle relative to a pump chamber surface and a second planar surface, connected to said first surface, extending substantially parallel to said pump chamber surface, and
    passively supporting said rotor using a passive axial magnetic bearing comprised of a housing magnet and a corresponding rotor magnet wherein magnetic fields of said housing magnet and said corresponding rotor magnet are oppositely aligned in the axial direction
    said hydrodynamic bearing and said passive axial magnetic bearing cooperating with each other so as to enhance axial stability of said rotor during said spinning of said rotor.

12. The method of pumping blood according to claim 11, wherein, said first surface is angled from said interior pump surface between about 0.5 degrees and about 3 degrees.

13. The method of pumping blood according to claim 11, wherein said each of said plurality of lifts is disposed on said rotor.

14. The method of pumping blood according to claim 11, wherein each of said plurality of lifts is disposed on said interior pump surface.

15. The method of pumping blood according to claim 14, wherein each of said plurality of lifts is formed integrally on said interior pump surface.

16. The method of pumping blood according to claim 11, wherein said plurality of lifts is comprised of at least three lifts.

17. The method of pumping blood according to claim 11, wherein said plurality of lifts constitutes a cumulative total area within a range of about 40% to 90% of said interior pump surface area.

18. The method of pumping blood according to claim 11, wherein the plurality of lifts are sized to produce an amount of force adequate to compensate for the sum of the net hydrodynamic/hydrostatic forces of said pump plus an attractive force between a motor magnet and back iron of said pump.

19. The method of pumping blood according to claim 11, wherein said plurality of lifts are sized and shaped to produce a hydrodynamic bearing when a clearance between said internal pump surface and said rotor is within a range of about 0.0002 inches to 0.001 inches.

20. The method of pumping blood according to claim 18, wherein said compensatory force produced by said plurality of lifts equals at least around 1.302 pounds.

21. The method of pumping blood according to claim 1, further comprising positioning said pump housing magnet and said rotor magnet to be offset from each other in an axial direction.

22. The method of pumping blood according to claim 11, further comprising positioning said housing magnet and said rotor magnet to be offset from each other in an axial direction.

\* \* \* \* \*